(12) United States Patent
Scheller et al.

(10) Patent No.: US 9,925,326 B2
(45) Date of Patent: *Mar. 27, 2018

(54) CANNULA INGRESS SYSTEM

(71) Applicant: Katalyst Surgical, LLC, Chesterfield, MO (US)

(72) Inventors: Gregg D Scheller, Wildwood, MO (US); Steven G Scheller, Wildwood, MO (US); Bradley S Niehoff, Lake St. Louis, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 365 days.

This patent is subject to a terminal disclaimer.

(21) Appl. No.: 14/820,082

(22) Filed: Aug. 6, 2015

(65) Prior Publication Data
US 2017/0021089 A1    Jan. 26, 2017

Related U.S. Application Data

(63) Continuation of application No. 14/803,557, filed on Jul. 20, 2015, now Pat. No. 9,775,943.

(51) Int. Cl.
*A61M 3/02* (2006.01)
*A61F 9/007* (2006.01)
*A61M 39/22* (2006.01)
*A61B 17/34* (2006.01)

(52) U.S. Cl.
CPC .......... *A61M 3/0283* (2013.01); *A61F 9/007* (2013.01); *A61M 39/22* (2013.01); *A61B 17/3421* (2013.01); *A61B 17/3462* (2013.01); *A61M 2205/582* (2013.01)

(58) Field of Classification Search
CPC . A61F 9/007; A61M 2205/582; A61M 39/22; A61M 3/0283; A61B 17/3462; A61B 17/3421
See application file for complete search history.

(56) References Cited

U.S. PATENT DOCUMENTS

| | | | |
|---|---|---|---|
| 4,553,957 A * | 11/1985 | Williams | ............ A61M 1/0084 604/43 |
| 5,921,998 A | 7/1999 | Tano et al. | |
| 6,575,989 B1 | 6/2003 | Scheller et al. | |
| 6,800,076 B2 | 10/2004 | Humayun | |

(Continued)

OTHER PUBLICATIONS

Steve Charles, Techniques and tools for dissection of epiretinal membranes, Graefe' Arch Clin Exp Ophthalmol, 241:347-352, 2003.

*Primary Examiner* — Bhisma Mehta
*Assistant Examiner* — Brandy S Lee
(74) *Attorney, Agent, or Firm* — Kevin P. Rollins

(57) ABSTRACT

A cannula ingress system may include a tip stabilization mechanism having a tip stabilization mechanism distal end and a tip stabilization mechanism proximal end, a fixation mechanism, a hypodermic tube having a hypodermic tube distal end and a hypodermic tube proximal end, and a tip having a tip distal end and a tip proximal end. The tip may be disposed within the hypodermic tube wherein the tip distal end extends from the hypodermic tube distal end. The fixation mechanism may be disposed within a fixation mechanism channel of the tip stabilization mechanism. The tip stabilization mechanism may be disposed over the tip and the hypodermic tube distal end.

20 Claims, 29 Drawing Sheets

(56) References Cited

U.S. PATENT DOCUMENTS

| | | |
|---|---|---|
| 2007/0282348 A1 | 12/2007 | Lumpkin |
| 2008/0183199 A1 | 7/2008 | Attinger |
| 2013/0197488 A1 | 8/2013 | Scheller et al. |
| 2014/0163363 A1 | 6/2014 | Scheller et al. |
| 2014/0172010 A1 | 6/2014 | Vezzu |
| 2014/0277110 A1 | 9/2014 | Scheller et al. |
| 2015/0088193 A1 | 3/2015 | Scheller et al. |

\* cited by examiner

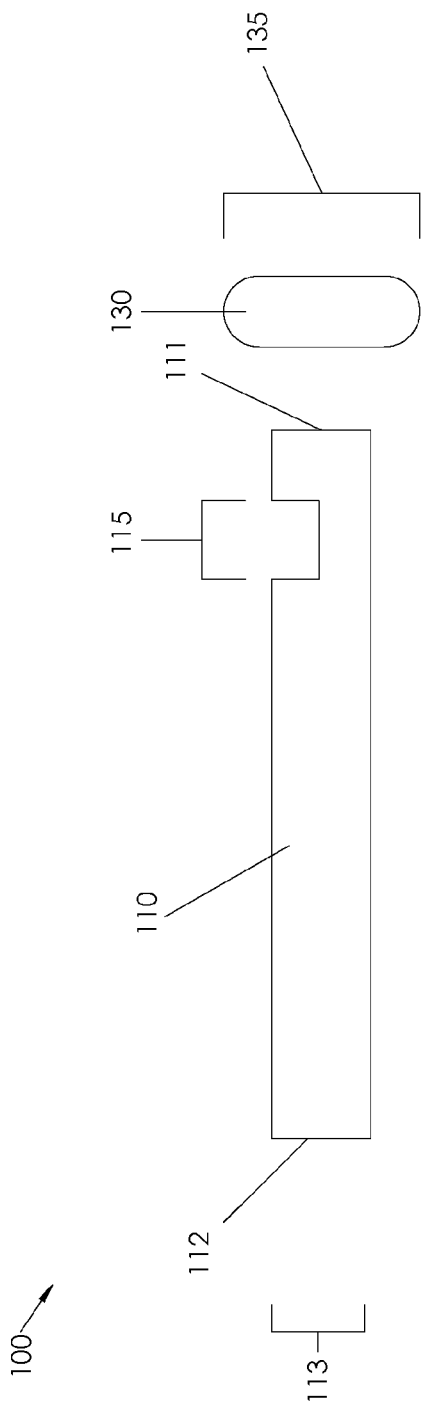
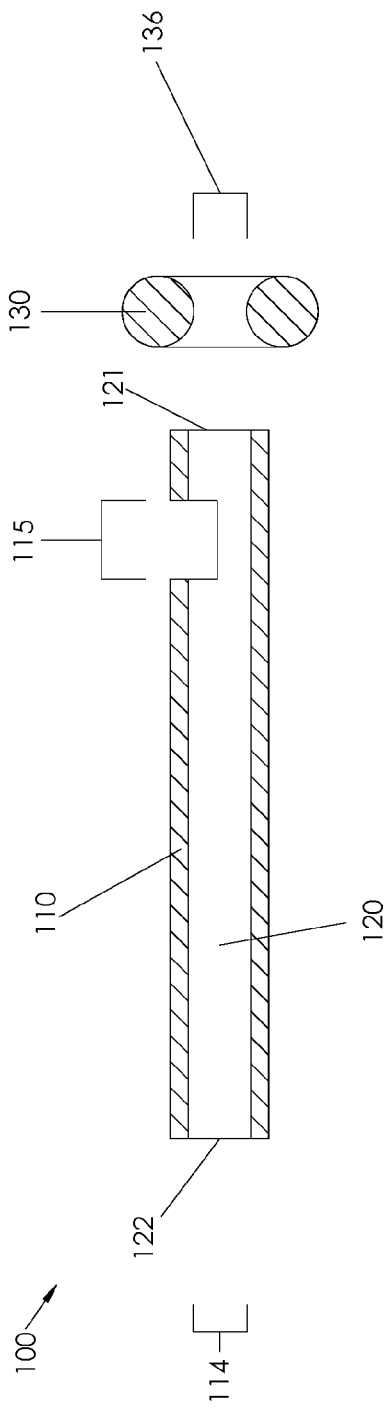
FIG. 1A
FIG. 1B

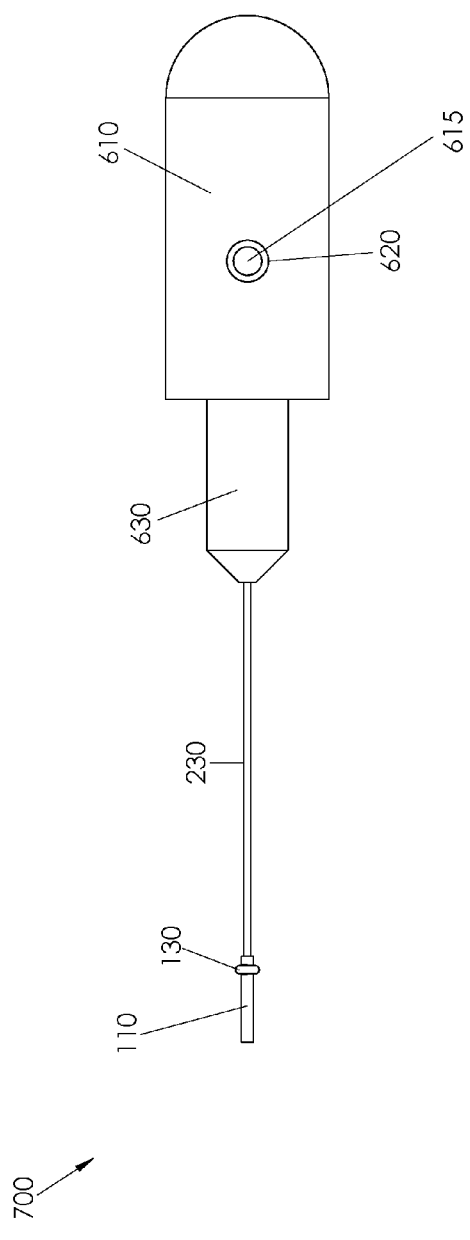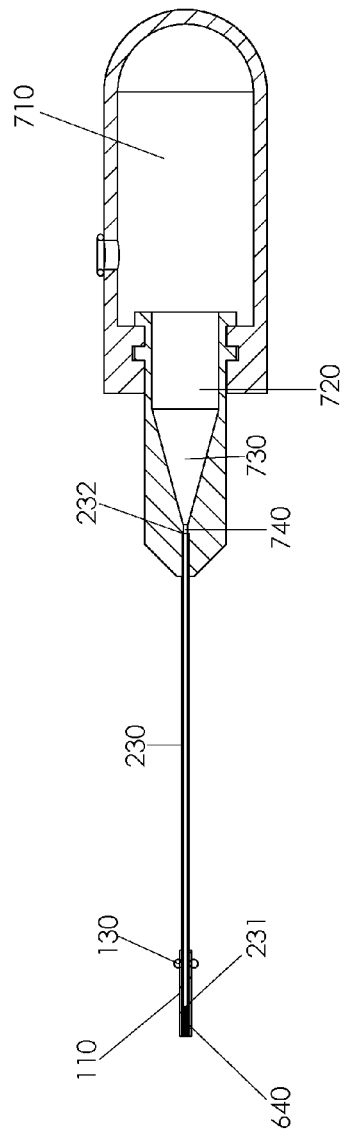
FIG. 7A
FIG. 7B

CANNULA INGRESS SYSTEM

CROSS-REFERENCE TO RELATED APPLICATIONS

This application is a continuation of prior application Ser. No. 14/803,557, filed Jul. 20, 2015.

FIELD OF THE INVENTION

The present disclosure relates to a medical device, and, more particularly, to a surgical instrument.

BACKGROUND OF THE INVENTION

Many ophthalmic surgical procedures in the posterior segment are performed through a cannula. For example, a surgeon may make an incision in the pars plana and then insert a cannula in the incision. The surgeon may then access the inner eye via the cannula. Ophthalmic surgical instruments having a soft, flexible tip may be difficult to insert into a cannula because the soft, flexible tip may deform as a surgeon attempts to ingress the cannula. For example, as a surgeon approaches a cannula to attempt a cannula ingress, a soft, flexible tip of an instrument must be precisely aligned with a cannula opening to prevent the soft, flexible tip from deforming.

BRIEF SUMMARY OF THE INVENTION

A cannula ingress system is presented. Illustratively, a cannula ingress system may comprise a tip stabilization mechanism having a tip stabilization mechanism distal end and a tip stabilization mechanism proximal end, a fixation mechanism, a hypodermic tube having a hypodermic tube distal end and a hypodermic tube proximal end, and a tip having a tip distal end and a tip proximal end. In one or more embodiments, the tip may be disposed within the hypodermic tube wherein the tip distal end extends from the hypodermic tube distal end. Illustratively, the fixation mechanism may be disposed within a fixation mechanism channel of the tip stabilization mechanism. In one or more embodiments, the tip stabilization mechanism may be disposed over the tip and the hypodermic tube distal end.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a tip stabilization system assembly;

FIGS. 7A and 7B are schematic diagrams illustrating an assembled irrigating and aspirating instrument;

DETAILED DESCRIPTION OF AN ILLUSTRATIVE EMBODIMENT

Figure 2:
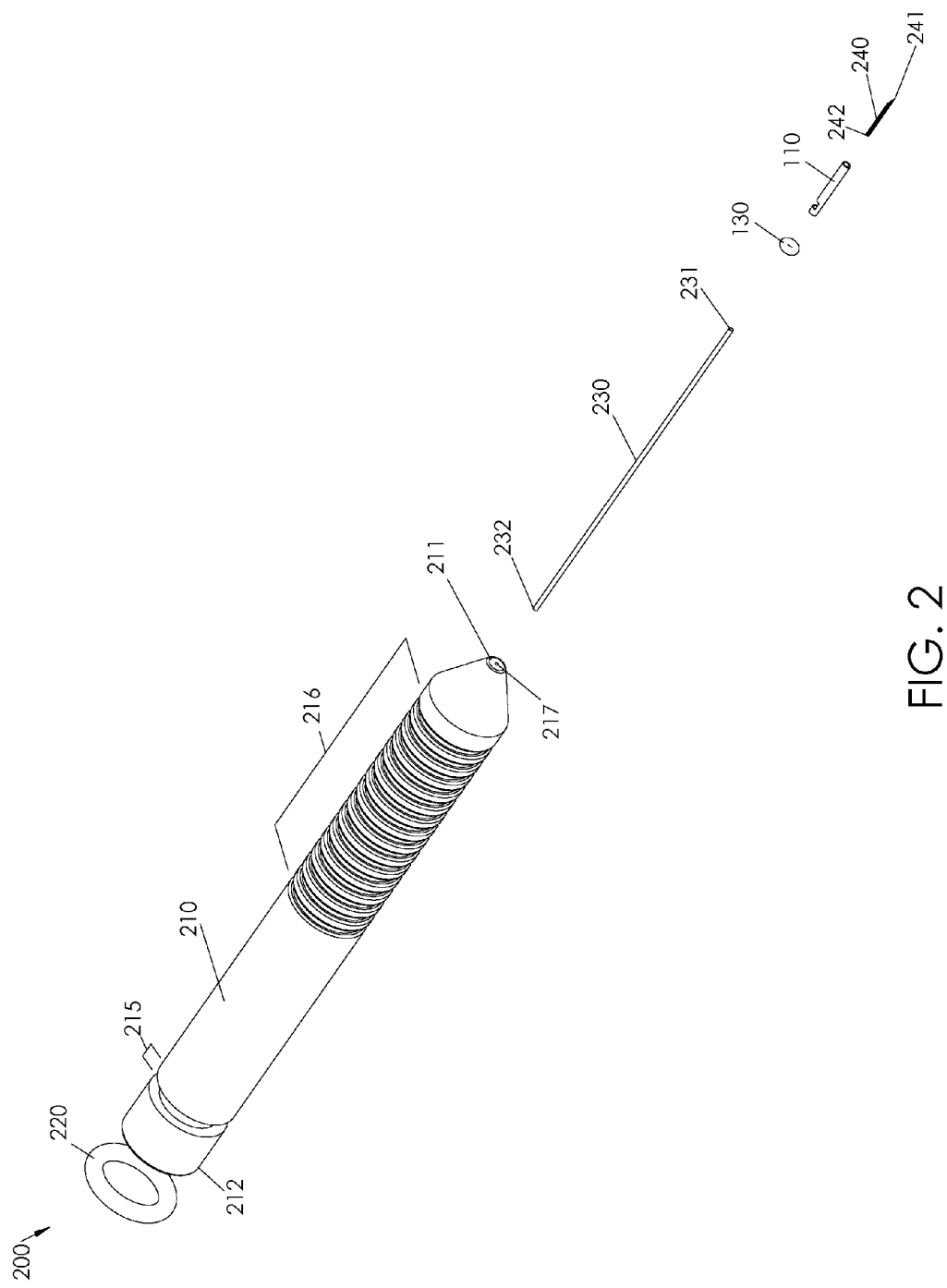
FIG. 2 is a schematic diagram illustrating an exploded view of an instrument assembly.

FIGS. 1A and 1B are schematic diagrams illustrating a tip stabilization system assembly 100. FIG. 1A illustrates a side view of a tip stabilization system assembly 100. In one or more embodiments, tip stabilization system assembly 100 may comprise a tip stabilization mechanism 110 and a fixation mechanism 130. Illustratively, tip stabilization mechanism 110 may comprise a tip stabilization mechanism distal end 111, a tip stabilization mechanism proximal end 112, a tip stabilization mechanism outer diameter 113, a tip stabilization mechanism inner diameter 114, and a fixation mechanism channel 115. In one or more embodiments, fixation mechanism channel 115 may have a width in a range of 0.01 to 0.05 inches, e.g., fixation mechanism channel 115 may have a width of 0.033 inches. Illustratively, fixation mechanism channel 115 may have a width of less than 0.01 inches or greater than 0.05 inches. In one or more embodiments, tip stabilization mechanism outer diameter 113 may be a distance in a range of 0.01 to 0.04 inches, e.g., tip stabilization mechanism outer diameter 113 may be a distance of 0.0226 inches. Illustratively, tip stabilization mechanism outer diameter 113 may be a distance of less than 0.01 inches or greater than 0.04 inches. In one or more embodiments, tip stabilization mechanism inner diameter 114 may be a distance in a range of 0.005 to 0.039 inches, e.g., tip stabilization mechanism inner diameter 114 may be a distance of 0.02 inches. Illustratively, tip stabilization mechanism inner diameter 114 may be a distance of less than 0.005 inches or greater than 0.039 inches. In one or more embodiments, tip stabilization mechanism 110 may have an overall length in a range of 0.2 to 0.4 inches, e.g., tip stabilization mechanism 110 may have an overall length of 0.3 inches. Illustratively, tip stabilization mechanism 110 may have an overall length of less than 0.2 inches or greater than 0.4 inches. In one or more embodiments, tip stabilization mechanism 110 may be manufactured from any suitable material, e.g., polymers, metals, metal alloys, etc., or from any combination of suitable materials. Illustratively, fixation mechanism 130 may comprise a fixation mechanism outer diameter 135 and a fixation mechanism inner diameter 136. In one or more embodiments, fixation mechanism outer diameter 135 may be greater than tip stabilization mechanism outer diameter 113, e.g., fixation mechanism outer diameter 135 may be a first distance and tip stabilization mechanism outer diameter 113 may be a second distance wherein the first distance is greater than the second distance. Illustratively, fixation mechanism outer diameter 135 may be less than tip stabilization mechanism outer diameter 113, e.g., fixation mechanism outer diameter 135 may be a first distance and tip stabilization mechanism outer diameter 113 may be a second distance wherein the first distance is less than the second distance. In one or more embodiments, fixation mechanism outer diameter 135 may be equal to tip stabilization mechanism outer diameter 113, e.g., fixation mechanism outer diameter 135 may be a first distance and tip stabilization mechanism outer diameter 113 may be a second distance wherein the first distance is equal to the second distance. Illustratively, fixation mechanism outer diameter 135 may be greater than tip stabilization mechanism inner diameter 114, e.g., fixation mechanism outer diameter 135 may be a first distance and tip stabilization mechanism inner diameter 114 may be a second distance wherein the first distance is greater than the second distance. In one or more embodiments, fixation mechanism outer diameter 135 may be less than tip stabilization mechanism inner diameter 114, e.g., fixation mechanism outer diameter 135 may be a first distance and tip stabilization mechanism inner diameter 114 may be a second distance wherein the first distance is less than the second distance. Illustratively, fixation mechanism outer diameter 135 may be equal to tip stabilization mechanism inner diameter 114, e.g., fixation mechanism outer diameter 135 may be a first distance and tip stabilization mechanism inner diameter 114 may be a second distance wherein the first distance is equal to the second distance. In one or more embodiments, fixation mechanism inner diameter 136 may be greater than tip stabilization mechanism outer diameter 113, e.g., fixation mechanism inner diameter 136 may be a first distance and tip stabilization mechanism outer diameter 136 may be a second distance where in the first distance is greater than the second distance. Illustratively, fixation mechanism inner diameter 136 may be less than tip stabilization mechanism outer diameter 113, e.g., fixation mechanism inner diameter 136 may be a first distance and tip stabilization mechanism outer diameter 136 may be a second distance where in the first distance is less than the second distance. In one or more embodiments, fixation mechanism inner diameter 136 may be equal to tip stabilization mechanism outer diameter 113, e.g., fixation mechanism inner diameter 136 may be a first distance and tip stabilization mechanism outer diameter 136 may be a second distance where in the first distance is equal to the second distance. Illustratively, fixation mechanism inner diameter 136 may be greater than tip stabilization mechanism inner diameter 114, e.g., fixation mechanism inner diameter 136 may be a first distance and tip stabilization mechanism inner diameter 114 may be a second distance wherein the first distance is greater than the second distance. In one or more embodiments, fixation mechanism inner diameter 136 may be less than tip stabilization mechanism inner diameter 114, e.g., fixation mechanism inner diameter 136 may be a first distance and tip stabilization mechanism inner diameter 114 may be a second distance wherein the first distance is less than the second distance. Illustratively, fixation mechanism inner diameter 136 may be equal to tip stabilization mechanism inner diameter 114, e.g., fixation mechanism inner diameter 136 may be a first distance and tip stabilization mechanism inner diameter 114 may be a second distance wherein the first distance is equal to the second distance. In one or more embodiments, fixation mechanism 130 may be manufactured from any suitable material, e.g., polymers, metals, metal alloys, etc., or from any combination of suitable materials. FIG. 1B illustrates a cross-sectional view of a tip stabilization system assembly 100. In one or more embodiments, fixation mechanism 130 may have a cross-sectional radius in a range of 0.005 to 0.03 inches, e.g., fixation mechanism 130 may have a cross-sectional radius of 0.015 inches. Illustratively, fixation mechanism 130 may have a cross-sectional radius of less than 0.005 inches or greater than 0.03 inches. In one or more embodiments, tip stabilization mechanism 110 may comprise an inner bore 120 having an inner bore distal end 121 and an inner bore proximal end 122. Illustratively, fixation mechanism 130 and tip stabilization mechanism 110 may be manufactured as a single component, e.g., fixation mechanism 130 may comprise a feature of tip stabilization mechanism 110. In one or more embodiments, tip stabilization mechanism 110 may comprise a tube and fixation mechanism 130 may comprise a discontinuity in inner bore 120, e.g., tube fixation mechanism 130 may comprise a portion of inner bore 120 having an inner diameter less than tip stabilization mechanism inner diameter 114.

FIG. 2 is a schematic diagram illustrating an exploded view of an instrument assembly 200. In one or more embodiments, an instrument assembly 200 may comprise a tip stabilization mechanism 110, a fixation mechanism 130, a handle 210, an identification ring 220, a hypodermic tube 230, and a membrane removing tip 240. Illustratively, handle 210 may comprise a handle distal end 211, a handle proximal end 212, an identification ring channel 215, a handle grip 216, and a hypodermic tube interface 217. In one or more embodiments, handle 210 may be manufactured from any suitable material, e.g., polymers, metals, metal alloys, etc., or from any combination of suitable materials. Illustratively, hypodermic tube 230 may comprise a hypodermic tube distal end 231 and a hypodermic tube proximal end 231. In one or more embodiments, hypodermic tube 230 may be manufactured at dimensions configured for performing microsurgical procedures, e.g., hypodermic tube 230 may be manufactured at dimensions configured for performing ophthalmic surgical procedures. Illustratively, hypodermic tube 230 may be 20 gauge, 23 gauge, 25 gauge, 27 gauge, etc. In one or more embodiments, hypodermic tube 230 may be manufactured from any suitable material, e.g., polymers, metals, metal alloys, etc., or from any combination of suitable materials. Illustratively, membrane removing tip 240 may comprise a membrane removing tip distal end 241 and a membrane removing tip proximal end 242. In one or more embodiments, membrane removing tip 240 may be manufactured from any suitable material, e.g., polymers, metals, metal alloys, etc., or from any combination of suitable materials. Illustratively, membrane removing tip 240 may be manufactured from silicone, e.g., biocompatible silicone.

Figure 3A:
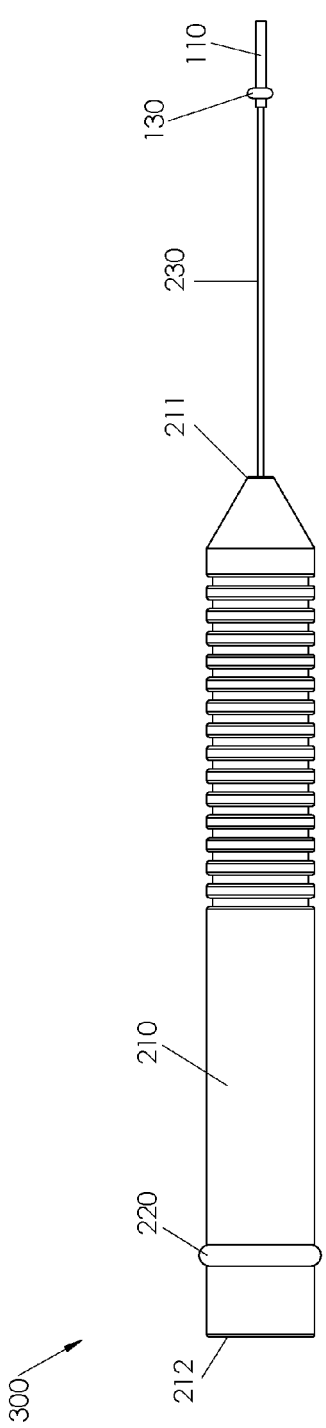
FIGS. 3A and 3B are schematic diagrams illustrating an assembled instrument.
Figure 3B:
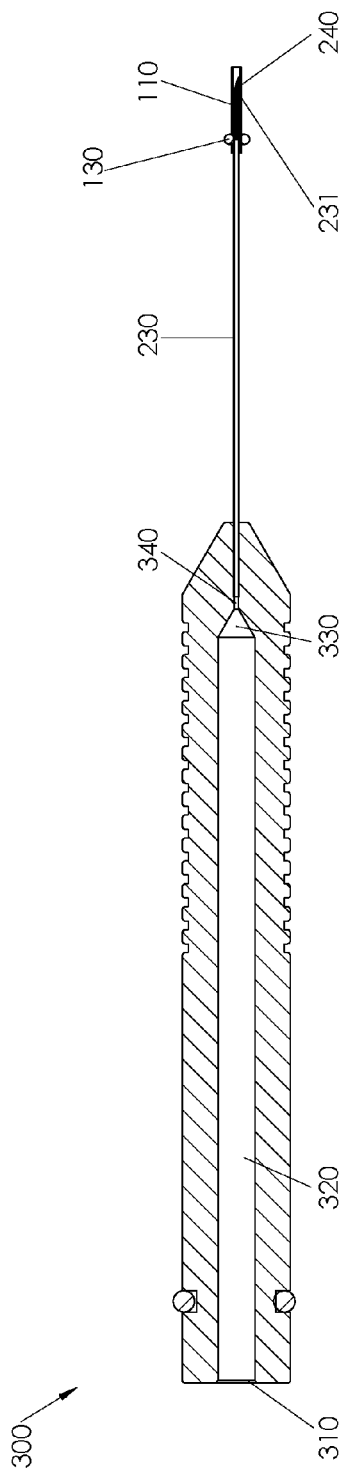

FIGS. 3A and 3B are schematic diagrams illustrating an assembled instrument 300. FIG. 3A illustrates a side view of an assembled instrument 300. In one or more embodiments, fixation mechanism 130 may be disposed over a portion of tip stabilization mechanism 110, e.g., fixation mechanism 130 may be disposed between tip stabilization mechanism distal end 111 and tip stabilization mechanism proximal end 112. Illustratively, a portion of fixation mechanism 130 may be disposed within a portion of tip stabilization mechanism 110, e.g., a portion of fixation mechanism 130 may be disposed within fixation mechanism channel 115. In one or more embodiments, a portion of fixation mechanism 130 may be disposed within inner bore 120. Illustratively, a portion of fixation mechanism 130 may be fixed to a portion of tip stabilization mechanism 110, e.g., fixation mechanism inner diameter 136 may be fixed to a portion of tip stabilization mechanism 110. In one or more embodiments, a portion of fixation mechanism 130 may be fixed to a portion of tip stabilization mechanism 110 by a force of friction or by any suitable fixation means, e.g., a portion of fixation mechanism 130 may be fixed to a portion of tip stabilization mechanism 110 by an adhesive, a weld, etc.

Illustratively, tip stabilization mechanism 110 may be disposed over a portion of hypodermic tube 230, e.g., tip stabilization mechanism distal end 111 may be disposed over hypodermic tube distal end 231. In one or more embodiments, a portion of hypodermic tube 230 may be disposed within inner bore 120, e.g., hypodermic tube distal end 231 may be disposed within inner bore 120. Illustratively, hypodermic tube 230 may be disposed within fixation mechanism 130, e.g., hypodermic tube 230 may be disposed within fixation mechanism inner diameter 136. In one or more embodiments, hypodermic tube 230 may not be disposed within fixation mechanism 130, e.g., a portion of hypodermic tube 230 may be disposed adjacent to a portion of fixation mechanism 130. Illustratively, fixation mechanism 130 may be configured to temporarily fix tip stabilization mechanism 110 in a position relative to hypodermic tube 230, e.g., a static friction force between fixation mechanism 130 and hypodermic tube 230 may be configured to temporarily fix tip stabilization mechanism 110 in a position relative to hypodermic tube 230. In one or more embodiments, a contact between a portion of fixation mechanism 130 and a portion of hypodermic tube 230 may be configured to temporarily fix tip stabilization mechanism 110 in a position relative to hypodermic tube 230. Illustratively, fixation mechanism 130 may be fixed to both tip stabilization mechanism 110 and hypodermic tube 230 wherein a static friction force between fixation mechanism 130 and hypodermic tube 230 may be configured to temporarily fix tip stabilization mechanism 110 in a position relative to hypodermic tube 230.

Illustratively, a portion of membrane removing tip 240 may be disposed within hypodermic tube 230, e.g., membrane removing tip proximal end 242 may be disposed within hypodermic tube distal end 231. In one or more embodiments, a portion of membrane removing tip 240 may be disposed within hypodermic tube 230 wherein a portion of membrane removing tip 240 extends from a portion of hypodermic tube 230, e.g., a portion of membrane removing tip 240 may be disposed within hypodermic tube 230 wherein membrane removing tip distal end 241 extends from hypodermic tube distal end 231. Illustratively, a portion of membrane removing tip 240 may be fixed within hypodermic tube 230, e.g., membrane removing tip proximal end 242 may be fixed within hypodermic tube 230. In one or more embodiments, a portion of membrane removing tip 240 may be fixed within hypodermic tube 230 by an adhesive or any suitable fixation means, e.g., a portion of membrane removing tip 240 may be fixed within hypodermic tube 230 by a friction fit, a weld, etc.

Illustratively, identification ring 220 may be disposed over a portion of handle 210, e.g., identification ring 220 may be disposed within identification ring channel 215. In one or more embodiments, identification ring 220 may be fixed to a portion of handle 210, e.g., identification ring 220 may be fixed within identification ring channel 215 by an adhesive, a force of friction, a weld, or any suitable fixation means. Illustratively, identification ring 220 may be configured to indicate one or more properties of assembled instrument 300 to a surgeon, a nurse, or a surgical technician, e.g., identification ring 220 may comprise a color or a marking configured to visually indicate a minimum cannula gauge size that hypodermic tube 230 may ingress to perform a surgical procedure. In one or more embodiments, identification ring 220 may be manufactured from a shape memory material, e.g., Nitinol. Illustratively, identification ring 220 may be manufactured from an elastomer material, e.g., a biocompatible elastomer material. In one or more embodiments, identification ring 220 may be manufactured from any suitable material, e.g., polymers, metals, metal alloys, etc., or from any combination of suitable materials.

FIG. 3B illustrates a cross-sectional view of an assembled instrument 300. In one or more embodiments, an assembled instrument 300 may comprise an inner chamber proximal taper 310, an inner chamber 320, an inner chamber distal taper 330, and a hypodermic tube housing 340. Illustratively, a portion of hypodermic tube 230 may be disposed within a portion of handle 210, e.g., a portion of hypodermic tube 230 may be disposed within a portion of handle 210 wherein the portion of hypodermic tube 230 may be adjacent to hypodermic tube interface 117. In one or more embodiments, a portion of hypodermic tube 230 may be disposed within hypodermic tube housing 340, e.g., hypodermic tube proximal end 232 may be disposed within hypodermic tube housing 340. In one or more embodiments, a portion of hypodermic tube 230 may be fixed within a portion of handle 210, e.g., a portion of hypodermic tube 230 may be fixed within hypodermic tube housing 340. Illustratively, a portion of hypodermic tube 230 may be fixed within hypodermic tube housing by an interference fit, an adhesive, a weld, etc. In one or more embodiments, a portion of hypodermic tube 230 may be fixed within a portion of handle 210 wherein hypodermic tube distal end 231 extends out from hypodermic tube housing 340.

Illustratively, membrane removing tip 240 may be disposed within hypodermic tube 230 and tip stabilization mechanism 110, e.g., membrane removing tip distal end 241 may be disposed between tip stabilization mechanism distal end 111 and tip stabilization mechanism proximal end 112. In one or more embodiments, membrane removing tip 240 may be disposed within hypodermic tube 230 and tip stabilization mechanism 110 wherein membrane removing tip proximal end 242 may be disposed between hypodermic tube distal end 231 and hypodermic tube proximal end 232. Illustratively, hypodermic tube 230 may be disposed within tip stabilization mechanism 110 wherein hypodermic tube distal end 231 is disposed between tip stabilization mechanism distal end 111 and tip stabilization mechanism proximal end 112.

Figure 4:
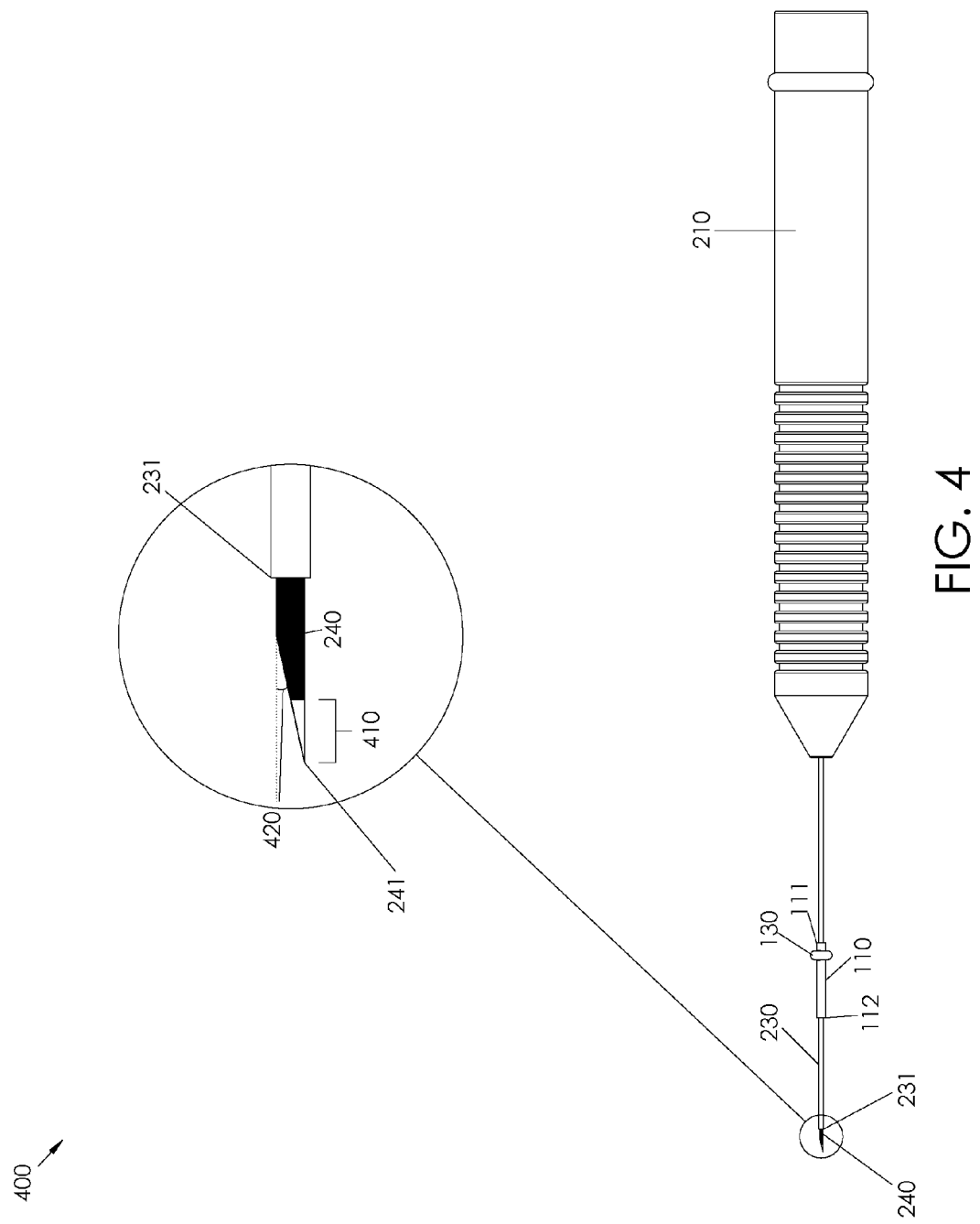
FIG. 4 is a schematic diagram illustrating an exposed membrane removing tip.

FIG. 4 is a schematic diagram illustrating an exposed membrane removing tip 400. In one or more embodiments, membrane removing tip 240 may be colored black, e.g., to enhance visualization of membrane removing tip 240. For example, membrane removing tip 240 may be manufactured from black silicone to enhance visualization of membrane removing tip 240. Illustratively, membrane removing tip 240 may be colored any color not contained within Johannes Itten's color wheel to enhance visualization of membrane removing tip 240, e.g., membrane removing tip 240 may be colored black or grey to enhance visualization of membrane removing tip 240. In one or more embodiments, an exposed membrane removing tip 400 may comprise an abrasive surface 410 and a membrane removing tip taper angle 420. Illustratively, membrane removing tip taper angle 420 may be an angle in a range of 10.0 to 60.0 degrees, e.g., membrane removing taper angle 420 may be an angle of 25.0 degrees. In one or more embodiments, membrane removing taper angle 420 may be an angle of less than 10.0 degrees or greater than 60.0 degrees.

In one or more embodiments, abrasive surface 410 may be configured to grasp a portion of a membrane, e.g., abrasive surface 410 may be configured to grasp a portion of an internal limiting membrane 410. Illustratively, a surgeon may maneuver a portion of abrasive surface 410 across a portion of a membrane, e.g., to raise a portion of the membrane. In one or more embodiments, abrasive surface 410 may be configured to grasp a portion of a first tissue disposed over a second tissue without damaging the second tissue. Illustratively, abrasive surface 410 may be configured to grasp a first tissue having a convex surface geometry disposed over a second tissue having a convex surface geometry without damaging the second tissue. In one or more embodiments, abrasive surface 410 may be manufactured by fixing particles, e.g., inert particles, to a portion of membrane removing tip 240. Illustratively, particles may be fixed to a portion of membrane removing tip 240, e.g., by an adhesive or any suitable fixation means. In one or more embodiments, particles may be fixed to a portion of membrane removing tip 240 by a biocompatible high temperature epoxy. Illustratively, particles may be fixed to a portion of membrane removing tip 240 by a biocompatible spectrally transparent epoxy. In one or more embodiments, a portion of membrane removing tip 240 may be coated by a material configured to facilitate adhesion of particles. Illustratively, a portion of membrane removing tip 240 may be coated by a material, e.g., silicon, and then particles may be fixed to the material, e.g., by an adhesive or any suitable fixation means. In one or more embodiments, abrasive surface 410 may be manufactured by fixing particles to a portion of membrane removing tip 240, e.g., particles may comprise diamond particles, sapphire particles, ruby particles, emerald particles, etc. Illustratively, abrasive surface 410 may be manufactured by fixing biocompatible particles to a portion of membrane removing tip 240. In one or more embodiments, abrasive surface 410 may be manufactured by fixing particles having particle diameters in a range of 5.0 to 25.0 micrometers to a portion of membrane removing tip 240, e.g., abrasive surface 410 may be manufactured by fixing particles having particle diameters of 15.0 micrometers to a portion of membrane removing tip 240. Illustratively, abrasive surface 410 may be manufactured by fixing particles having particle diameters less than 5.0 micrometers or greater than 25.0 micrometers to a portion of membrane removing tip 240. In one or more embodiments, membrane removing tip 240 may be colored black, e.g., to enhance visualization of abrasive surface 410. For example, membrane removing tip 240 may be manufactured from black silicone to enhance visualization of abrasive surface 410. Illustratively, membrane removing tip 240 may be colored any color not contained within Johannes Itten's color wheel to enhance visualization of abrasive surface 410, e.g., membrane removing tip 240 may be colored black or grey to enhance visualization of abrasive surface 410.

In one or more embodiments, abrasive surface 410 may be manufactured by modifying membrane removing tip 240, e.g., by an electric discharge machine. Illustratively, abrasive surface 410 may be manufactured by actuating a portion of membrane removing tip 240 relative to a wire of an electric discharge machine, e.g., to form a plurality of micropillars. In one or more embodiments, abrasive surface 410 may be manufactured by actuating a wire of an electric discharge machine relative to a portion of membrane removing tip 240, e.g., to form a plurality of micropillars. Illustratively, membrane removing tip 240 may be modified, e.g., by an electric discharge machine, wherein one or more portions of membrane removing tip 240 comprise a plurality of micropillars. Illustratively, abrasive surface 410 may be manufactured by modifying membrane removing tip 240, e.g., by laser ablation. In one or more embodiments, abrasive surface 410 may be manufactured by modifying membrane removing tip 240, e.g., by femtosecond laser ablation. Illustratively, abrasive surface 410 may be manufactured by applying laser energy to a portion of membrane removing tip 240 wherein the laser energy is applied in geometric patterns configured to fabricate micropillars on a surface of membrane removing tip 240, e.g., the laser energy may be applied in concentric circles, polygons, etc. In one or more embodiments, abrasive surface 410 may be manufactured by applying laser energy to a portion of membrane removing tip 240 wherein the laser energy is applied repeatedly in geometric patterns configured to fabricate micropillars on a surface of membrane removing tip 240, e.g., the laser energy may be repeatedly applied in concentric circles, polygons, etc. Illustratively, membrane removing tip 240 may be modified, e.g., by laser ablation, wherein one or more portions of membrane removing tip 240 comprise a plurality of micropillars. In one or more embodiments, membrane removing tip 240 may be modified wherein one or more portions of membrane removing tip 240 comprise a plurality of micropillars and then membrane removing tip 240 may be modified to manufacture membrane removing tip 240. Illustratively, one or more portions of membrane removing tip 240 may comprise a plurality of micropillars. In one or more embodiments, membrane removing tip 240 may be modified, e.g., by an electric discharge machine, to manufacture membrane removing tip 240 and then membrane removing tip 240 may be modified, e.g., by laser ablation, wherein one or more portions of membrane removing tip 240 comprise a plurality of micropillars.

Illustratively, abrasive surface 410 may be manufactured by modifying membrane removing tip 240, e.g., by deep reactive-ion etching. In one or more embodiments, abrasive surface 410 may be manufactured by modifying membrane removing tip 240, e.g., by the Bosch process of time-multiplexed etching. Illustratively, abrasive surface 410 may be manufactured by exposing a portion of membrane removing tip 240 to repeated cycles of isotropic plasma etching followed by deposition of a chemically inert passivation layer to fabricate a plurality of micropillars on a surface of membrane removing tip 240. In one or more embodiments, abrasive surface 410 may be manufactured by fabricating a plurality of micropillars on a substrate and then fixing the substrate to a portion of membrane removing tip 240. Illustratively, membrane removing tip 240 may be modified, e.g., by deep reactive-ion etching, wherein one or more portions of membrane removing tip 240 comprise a plurality of micropillars. In one or more embodiments, membrane removing tip 240 may be modified wherein one or more portions of membrane removing tip 240 comprise a plurality of micropillars and then membrane removing tip 240 may be modified to manufacture membrane removing tip 240. Illustratively, one or more portions of membrane removing tip 240 may comprise a plurality of micropillars. In one or more embodiments, membrane removing tip 240 may be modified, e.g., by an electric discharge machine, to manufacture membrane removing tip 240 and then membrane removing tip 240 may be modified, e.g., by deep reactive-ion etching, wherein one or more portions of membrane removing tip 240 comprise a plurality of micropillars.

Illustratively, abrasive surface 410 may comprise a plurality of micropillars, e.g., abrasive surface 410 may comprise one or more micropillar arrays. In one or more embodiments, abrasive surface 410 may comprise a plurality of micropillars having micropillar diameters in a range of 5.0 to 25.0 micrometers, e.g., abrasive surface 410 may comprise a plurality of micropillars having micropillar diameters of 15.0 micrometers. In one or more embodiments, abrasive surface 410 may comprise a plurality of micropillars having micropillar diameters less than 5.0 micrometers or greater than 25.0 micrometers. Illustratively, abrasive surface 410 may comprise a plurality of micropillars having micropillar heights in a range of 0.25 to 3.0 micrometers, e.g., abrasive surface 410 may comprise a plurality of micropillars having micropillar heights of 2.25 micrometers. In one or more embodiments, abrasive surface 410 may comprise a plurality of micropillars having micropillar heights less than 0.25 micrometers or greater than 3.0 micrometers. Illustratively, abrasive surface 410 may comprise a plurality of micropillars having micropillar heights in a range of 10.0 to 95.0 percent of the average thickness of an internal limiting membrane, e.g., abrasive surface 410 may comprise a plurality of micropillars having micropillar heights of 80.0 percent of the average thickness of an internal limiting membrane. In one or more embodiments, abrasive surface 410 may comprise a plurality of micropillars having micropillar orientations normal to a portion of a surface of membrane removing tip 240. Illustratively, abrasive surface 410 may comprise a plurality of micropillars having micropillar orientations at an angle relative to a portion of a surface of membrane removing tip 240. In one or more embodiments, abrasive surface 410 may comprise a plurality of micropillars having micropillar orientations at an angle in a range of 60.0 to 89.0 degrees relative to a portion of a surface of membrane removing tip 240, e.g., abrasive surface 410 may comprise a plurality of micropillars having micropillar orientations at an angle of 85.0 degrees relative to a portion of a surface of membrane removing tip 240. Illustratively, abrasive surface 410 may comprise a plurality of micropillars having micropillar orientations at an angle less than 60.0 degrees or greater than 89.0 degrees relative to a portion of a surface of membrane removing tip 240.

Figure 5A:
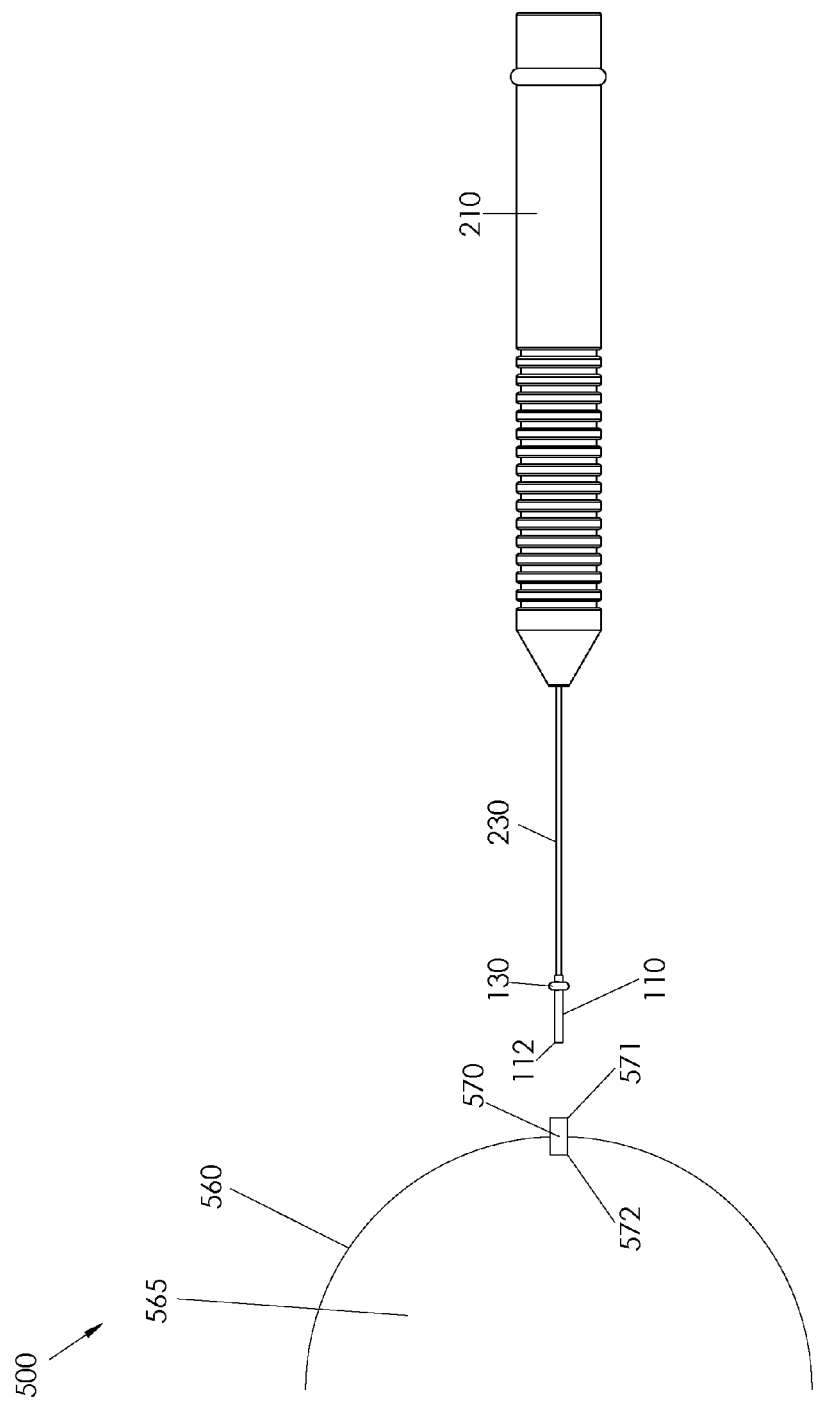
FIGS. 5A, 5B, 5C, 5D, 5E, and 5F are schematic diagrams illustrating a portion of a surgical procedure.

FIGS. 5A, 5B, 5C, 5D, 5E, and 5F are schematic diagrams illustrating a portion of a surgical procedure. FIG. 5A illustrates a cannula approach 500. Illustratively, a surgeon may maneuver an assembled instrument 300 towards an eye 560 to perform a portion of a surgical procedure, e.g., a surgeon may maneuver an assembled instrument 300 towards a cannula 570 to perform a portion of a surgical procedure. In one or more embodiments, cannula 570 may comprise a cannula distal end 571 and a cannula proximal end 572. Illustratively, cannula 570 may be disposed within an incision in eye 560, e.g., cannula 570 may be disposed within an incision in eye 560 wherein cannula distal end 571 extends out from an outer surface of eye 560 and cannula proximal end 572 is disposed within an inner eye 565. In one or more embodiments, a cannula approach 500 may comprise an attempt to guide tip stabilization mechanism proximal end 112 towards cannula distal end 571.

Figure 5B:
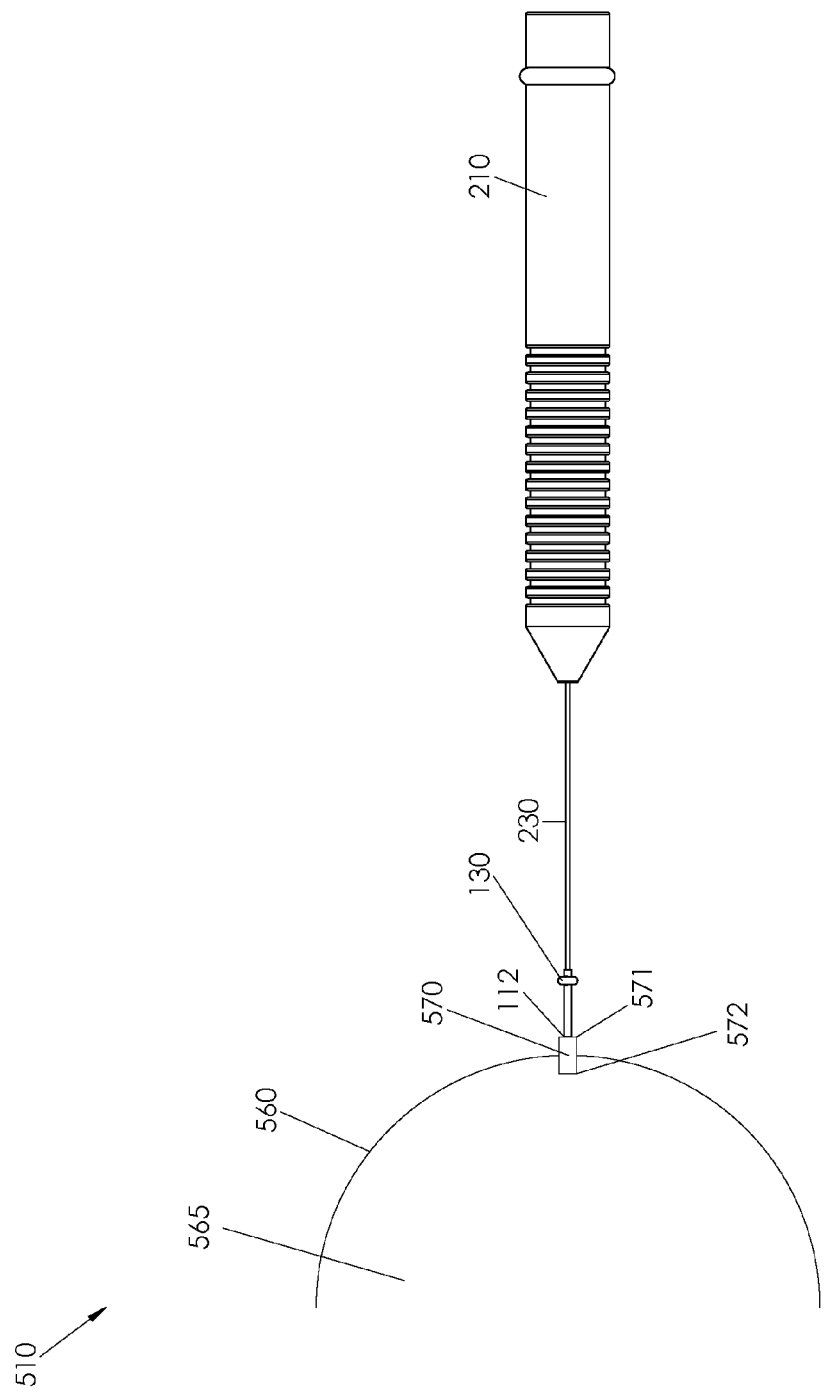

FIG. 5B illustrates a cannula contact 510. Illustratively, a surgeon may approach cannula 570 with assembled instrument 300 until a portion of assembled instrument 300 contacts a portion of cannula 570, e.g., a surgeon may approach cannula 570 with assembled instrument 300 until tip stabilization mechanism proximal end 112 contacts cannula distal end 571. In one or more embodiments, a cannula contact 510 may comprise a contact between tip stabilization mechanism proximal end 112 and cannula distal end 571. Illustratively, a cannula contact 510 may be configured to apply a force to fixation mechanism 130, e.g., a cannula contact 510 may apply a normal force to tip stabilization mechanism 110. In one or more embodiments, an application of a normal force to tip stabilization mechanism 110 may be configured to retract tip stabilization mechanism 110 relative to hypodermic tube 230, e.g., a normal force applied to tip stabilization mechanism 110 may be greater than a static friction force between fixation mechanism 130 and hypodermic tube 230. Illustratively, an application of a normal force to tip stabilization mechanism 110 may not be configured to retract tip stabilization mechanism 110 relative to hypodermic tube 230, e.g., a normal force applied to tip stabilization mechanism 110 may be less than a static friction force between fixation mechanism 130 and hypodermic tube 230.

Figure 5C:
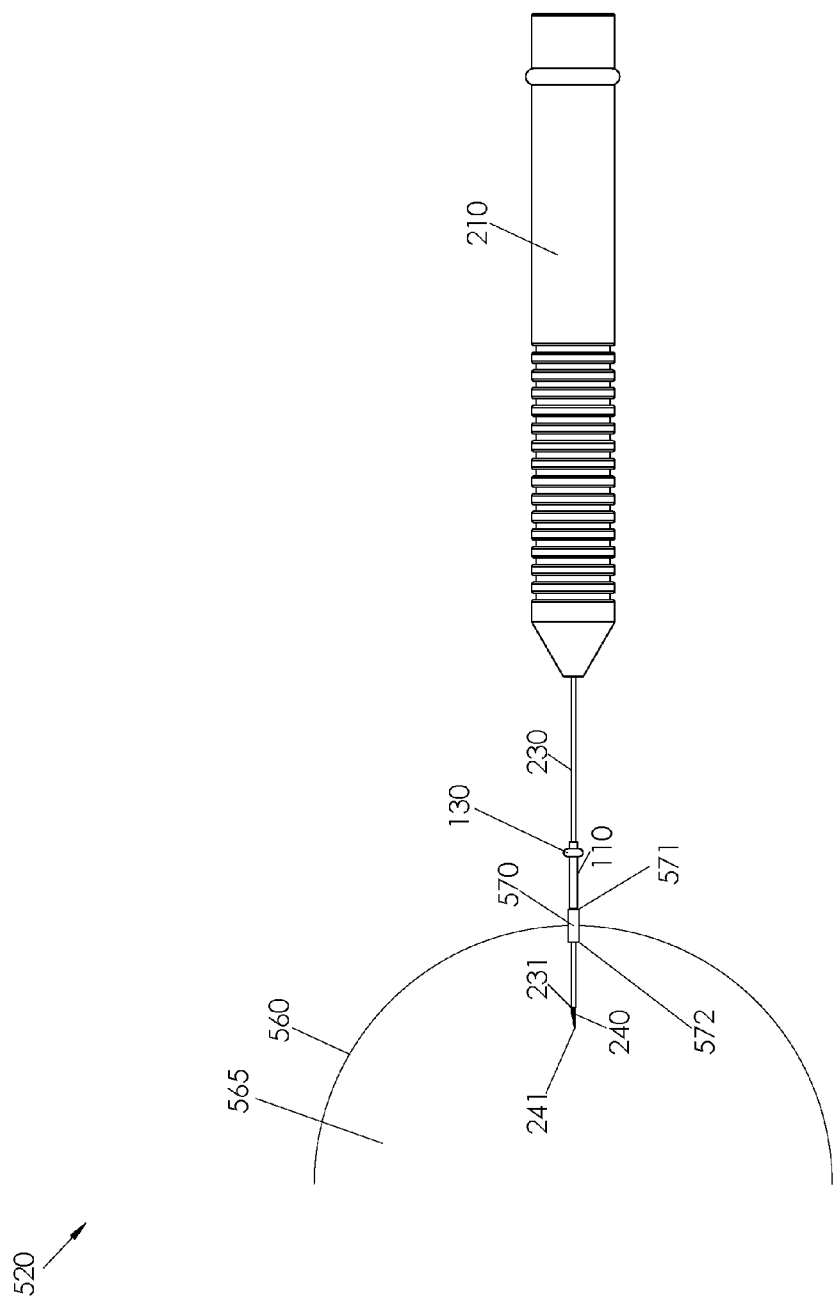

FIG. 5C illustrates a partial membrane removing tip insertion 520. Illustratively, a surgeon may guide a portion of assembled instrument 300 into cannula 570, e.g., by advancing handle 210 towards eye 560 after a cannula contact 510. In one or more embodiments, advancing handle 210 towards eye 560 after a cannula contact 510 may be configured to apply a force to tip stabilization mechanism proximal end 112. Illustratively, an application of a force to tip stabilization mechanism proximal end 112 may be configured to actuate tip stabilization mechanism 110 relative to hypodermic tube 230, e.g., an application of a force to tip stabilization mechanism proximal end 112 may be configured to actuate tip stabilization mechanism distal end 111 towards handle distal end 211. In one or more embodiments, advancing handle 210 towards eye 560 after a cannula contact 510 may be configured to apply a force to tip stabilization mechanism 110 that is greater than a static friction force between fixation mechanism 130 and hypodermic tube 230. Illustratively, advancing handle 210 towards eye 560 after a cannula contact 510 may be configured to retract tip stabilization mechanism 110 and fixation mechanism 130 relative to hypodermic tube 230. In one or more embodiments, advancing handle 210 towards eye 560 after a cannula contact 510 may actuate membrane removing tip distal end 241 into cannula distal end 571. Illustratively, advancing handle 210 towards eye 560 after a cannula contact 510 may be configured to actuate hypodermic tube distal end 231 into cannula distal end 571. In one or more embodiments, advancing handle 210 towards eye 560 after a cannula contact 510 may be configured to actuate membrane removing tip distal end 271 out from cannula proximal end 572. Illustratively, advancing handle 210 towards eye 560 after a cannula contact 510 may be configured to actuate hypodermic tube distal end 231 out from cannula proximal end 572. In one or more embodiments, advancing handle 210 towards eye 560 after a cannula contact 510 may be configured to actuate membrane removing tip 240 into inner eye 565.

Figure 5D:
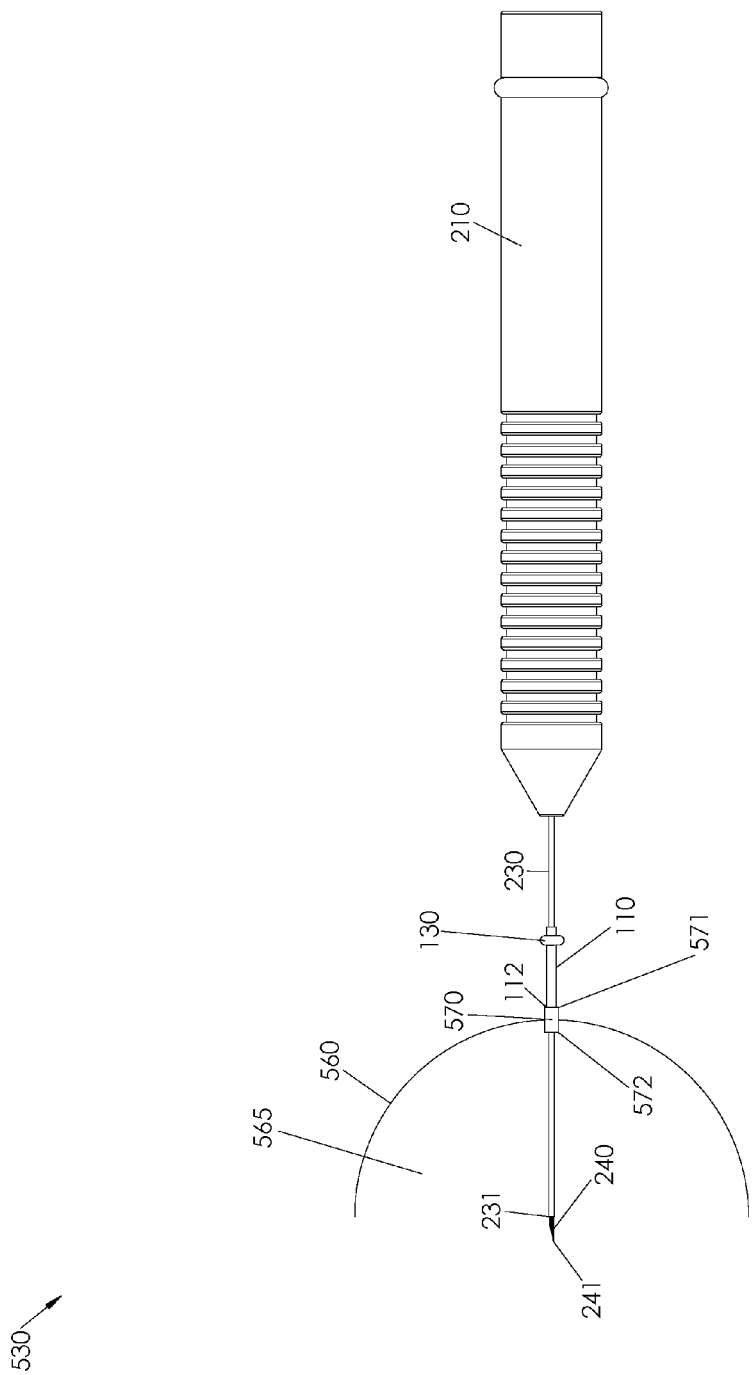

FIG. 5D illustrates a complete membrane removing tip insertion 530. In one or more embodiments, advancing handle 210 towards eye 560 after a partial membrane removing tip insertion 520 may be configured to apply a force to tip stabilization mechanism proximal end 112. Illustratively, an application of a force to tip stabilization mechanism proximal end 112 may be configured to actuate tip stabilization mechanism 110 relative to hypodermic tube 230, e.g., an application of a force to tip stabilization mechanism proximal end 112 may be configured to actuate tip stabilization mechanism distal end 111 towards handle distal end 211. In one or more embodiments, advancing handle 210 towards eye 560 after a partial membrane removing tip insertion 520 may be configured to apply a force to tip stabilization mechanism 110 that is greater than a static friction force between fixation mechanism 130 and hypodermic tube 230. Illustratively, advancing handle 210 towards eye 560 after a partial membrane removing tip insertion 520 may be configured to retract tip stabilization mechanism 110 and fixation mechanism 130 relative to hypodermic tube 230. In one or more embodiments, advancing handle 210 towards eye 560 after a partial membrane removing tip insertion 520 may be configured to actuate membrane removing tip 240 within inner eye 565.

Figure 5E:
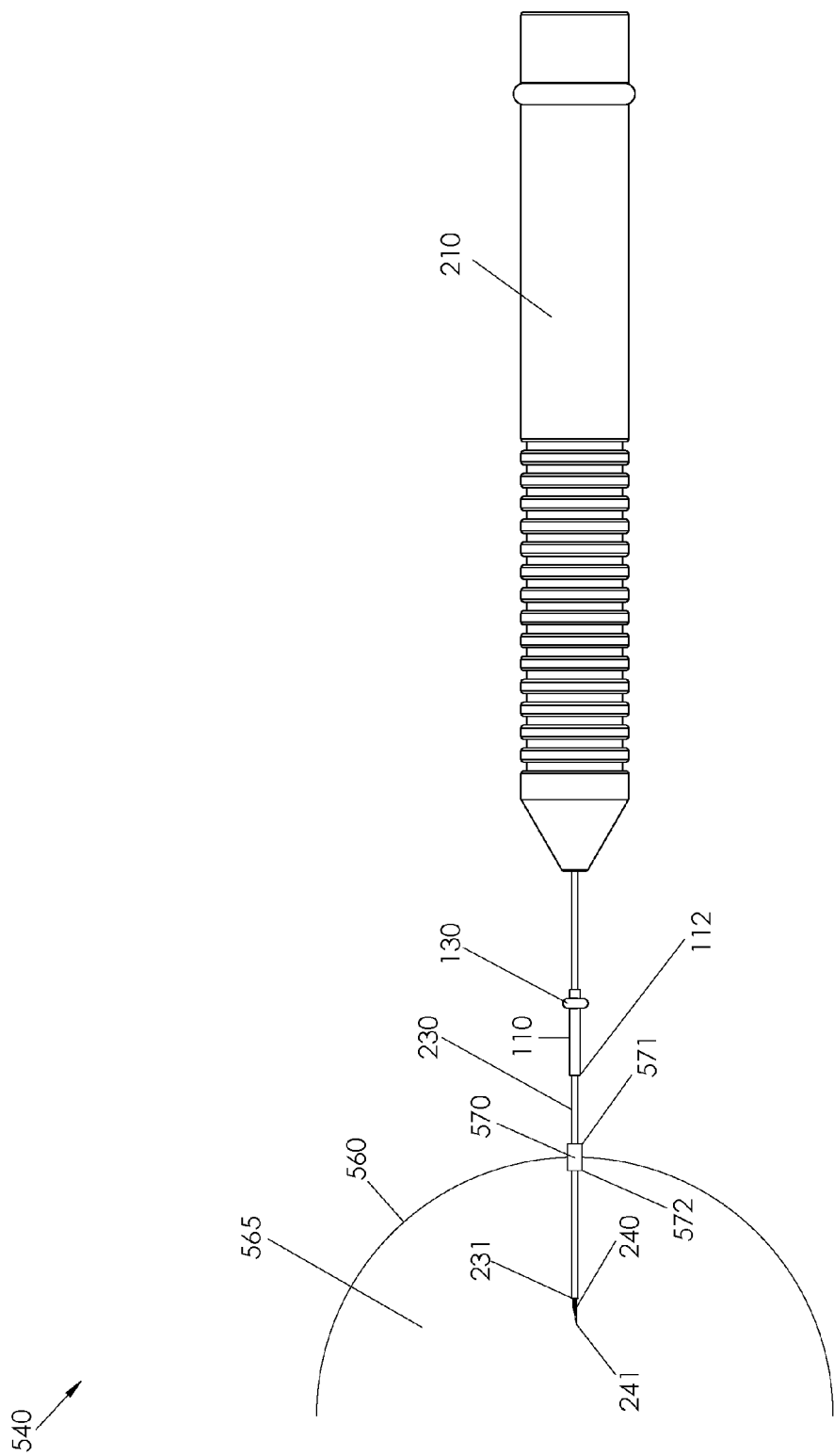

FIG. 5E illustrates a partial membrane removing tip extraction 540. Illustratively, a surgeon may guide a portion of assembled instrument 300 out from cannula 570, e.g., by retracting handle 210 away from eye 560 after a complete membrane removing tip insertion 530. In one or more embodiments, retracting handle 210 away from eye 560 may be configured to reduce a force applied to tip stabilization mechanism 110. Illustratively, reducing a force applied to tip stabilization mechanism 110 may be configured to fix tip stabilization mechanism 110 and fixation mechanism 130 in a position relative to hypodermic tube 230. In one or more embodiments, a surgeon may use a distance between tip stabilization mechanism proximal end 112 and cannula distal end 571 as a depth gauge to evaluate a risk associated with a surgical procedure, e.g., during a difficult membrane removal, a surgeon may be concerned about damaging a patient's retinal tissue. Illustratively, a surgeon may use a distance between tip stabilization mechanism proximal end 112 and cannula distal end 571 as a depth gauge to compare a depth into the posterior segment of inner eye 565 of a particular portion of a surgical procedure with a depth into the posterior segment of inner eye 565 of a prior portion of a surgical procedure. For example, if a surgeon notices that a first attempt to raise a membrane from a retinal tissue causes damage to the retinal tissue, then the surgeon may note a depth of the first attempt to raise the membrane by observing a relative distance between tip stabilization mechanism proximal end 112 and cannula distal end 571. Illustratively, the surgeon may make a second attempt to raise the membrane from the retinal tissue at a depth less than the depth of the first attempt to raise the membrane from the retinal tissue by preventing a contact between tip stabilization mechanism proximal end 112 and cannula distal end 571.

Figure 5F:
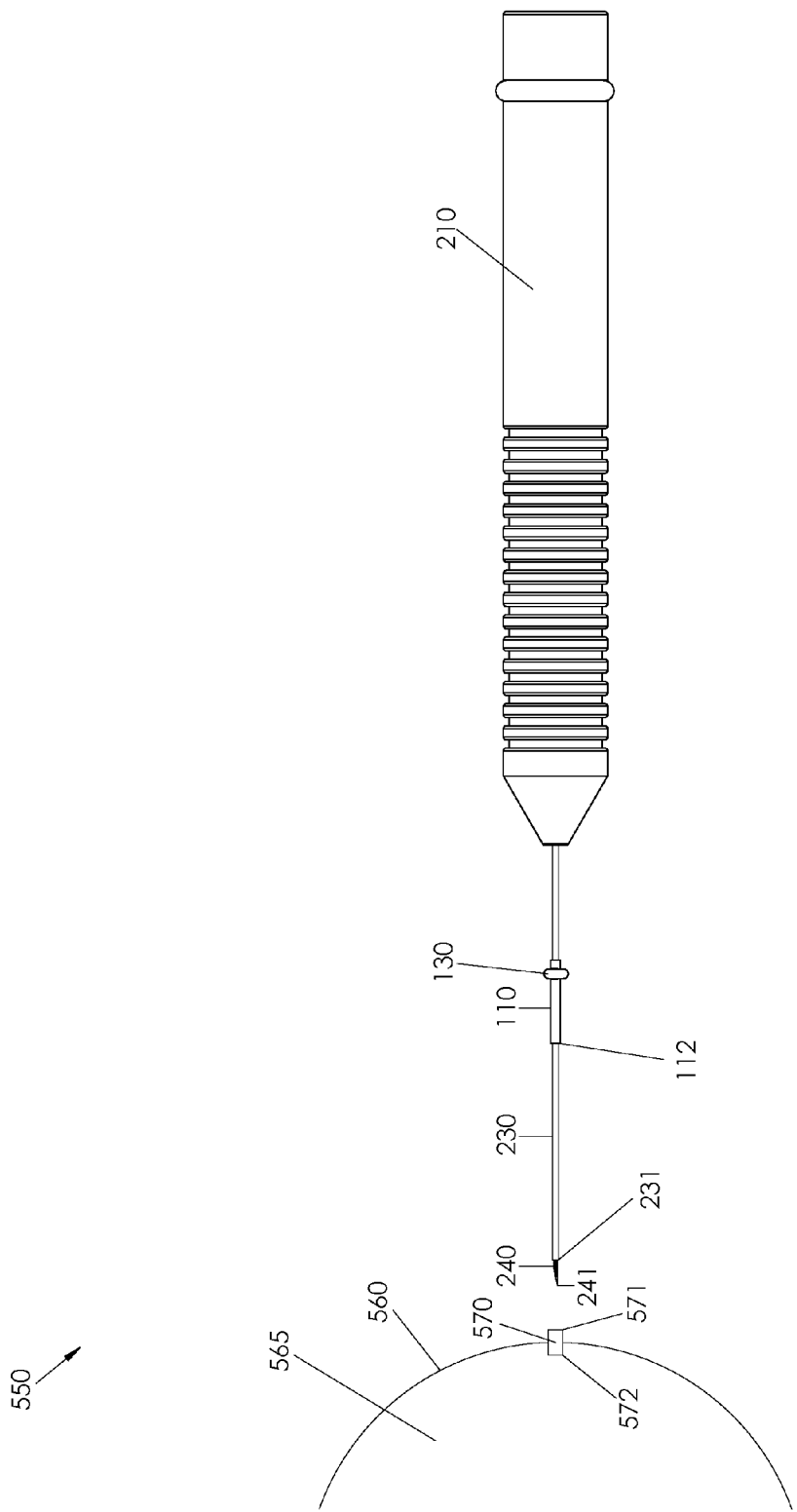

FIG. 5F illustrates a complete membrane removing tip extraction 550. Illustratively, a surgeon may guide a portion of assembled instrument 300 out from cannula 570, e.g., by retracting handle 210 away from eye 560 after a partial membrane removing tip extraction 540. In one or more embodiments, retracting handle 210 away from eye 560 after a partial membrane removing tip extraction 540 may be configured to extract membrane removing tip 240 from cannula 570. Illustratively, after a complete membrane removing tip extraction 550, tip stabilization mechanism 110 may be fixed in a position relative to hypodermic tube 230, e.g., assembled instrument 300 may comprise an exposed membrane removing tip 400 after a complete membrane removing tip extraction 550. In one or more embodiments, a surgeon may prepare assembled instrument 300 for a second cannula approach 500 after a complete membrane removing tip extraction 550 by grasping tip stabilization mechanism 110 and actuating tip stabilization mechanism 110 relative to hypodermic tube 230 towards membrane removing tip 240. Illustratively, a surgeon may prepare assembled instrument 300 for a second cannula approach 500 after a complete membrane removing tip extraction 550 by actuating tip stabilization mechanism 110 over membrane removing tip 240.

Figure 6:
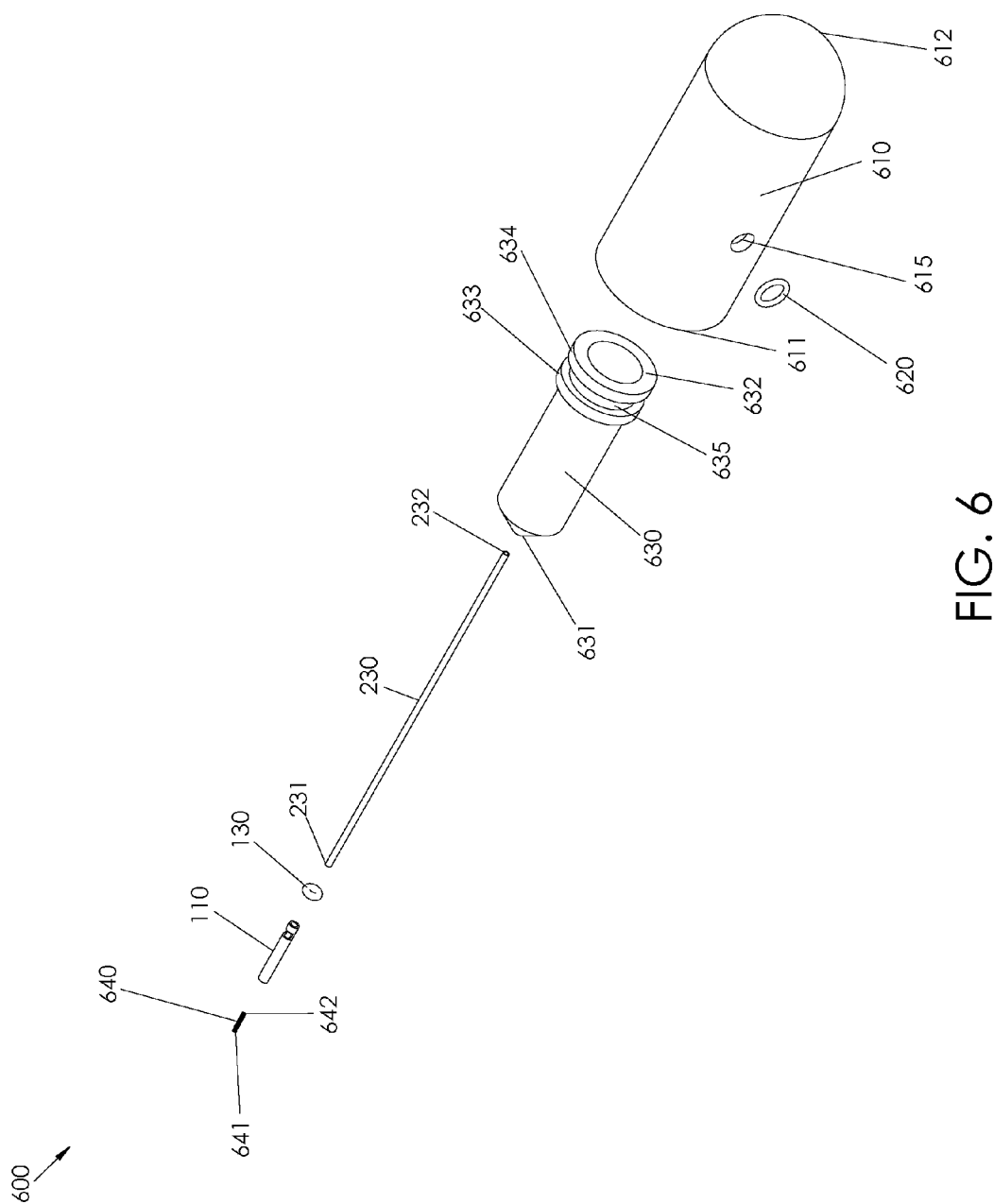
FIG. 6 is a schematic diagram illustrating an exploded view of an irrigating and aspirating instrument assembly.

FIG. 6 is a schematic diagram illustrating an exploded view of an irrigating and aspirating instrument assembly 600. In one or more embodiments, an irrigating and aspirating instrument assembly may comprise a tip stabilization mechanism 110, a fixation mechanism 130, a hypodermic tube 230, a flow control mechanism 610, a pressure vent tactile locater 620, a fluid guide 630, and an irrigating and aspirating tip 640. Illustratively, flow control mechanism 610 may comprise a flow control mechanism distal end 611, a flow control mechanism proximal end 612, and a pressure vent 615. In one or more embodiments, flow control mechanism 610 may be manufactured from any suitable material, e.g., polymers, metals, metal alloys, etc., or from any combination of suitable materials. Illustratively, fluid guide 630 may comprise a fluid guide distal end 631, a fluid guide proximal end 632, a distal locking lip 633, a proximal locking lip 634, and a locking depression 635. In one or more embodiments, fluid guide 630 may be manufactured from any suitable material, e.g., polymers, metals, metal alloys, etc., or from any combination of suitable materials. Illustratively, irrigating and aspirating tip 640 may comprise an irrigating and aspirating tip distal end 641 and an irrigating and aspirating tip proximal end 642. In one or more embodiments, irrigating and aspirating tip 640 may be manufactured from any suitable material, e.g., polymers, metals, metal alloys, etc., or from any combination of suitable materials. Illustratively, irrigating and aspirating tip 640 may be manufactured from silicone, e.g., biocompatible silicone. In one or more embodiments, irrigating and aspirating tip 640 may comprise an inner lumen for irrigation of fluids. Illustratively, irrigating and aspirating tip 640 may comprise an inner lumen for aspiration of fluids. In one or more embodiments, irrigating and aspirating tip 640 may comprise an inner lumen for irrigation of fluids and for aspiration of fluids.

FIGS. 7A and 7B are schematic diagrams illustrating an assembled irrigating and aspirating instrument 700. FIG. 7A illustrates a top view of an assembled irrigating and aspirating instrument 700. In one or more embodiments, fixation mechanism 130 may be disposed over a portion of tip stabilization mechanism 110, e.g., fixation mechanism 130 may be disposed between tip stabilization mechanism distal end 111 and tip stabilization mechanism proximal end 112. Illustratively, a portion of fixation mechanism 130 may be disposed within a portion of tip stabilization mechanism 110, e.g., a portion of fixation mechanism 130 may be disposed within fixation mechanism channel 115. In one or more embodiments, a portion of fixation mechanism 130 may be disposed within inner bore 120. Illustratively, a portion of fixation mechanism 130 may be fixed to a portion of tip stabilization mechanism 110, e.g., fixation mechanism inner diameter 136 may be fixed to a portion of tip stabilization mechanism 110. In one or more embodiments, a portion of fixation mechanism 130 may be fixed to a portion of tip stabilization mechanism 110 by a force of friction or by any suitable fixation means, e.g., a portion of fixation mechanism 130 may be fixed to a portion of tip stabilization mechanism 110 by an adhesive, a weld, etc.

Illustratively, tip stabilization mechanism 110 may be disposed over a portion of hypodermic tube 230, e.g., tip stabilization mechanism distal end 111 may be disposed over hypodermic tube distal end 231. In one or more embodiments, a portion of hypodermic tube 230 may be disposed within inner bore 120, e.g., hypodermic tube distal end 231 may be disposed within inner bore 120. Illustratively, hypodermic tube 230 may be disposed within fixation mechanism 130, e.g., hypodermic tube 230 may be disposed within fixation mechanism inner diameter 136. In one or more embodiments, hypodermic tube 230 may not be disposed within fixation mechanism 130, e.g., a portion of hypodermic tube 230 may be disposed adjacent to a portion of fixation mechanism 130. Illustratively, fixation mechanism 130 may be configured to temporarily fix tip stabilization mechanism 110 in a position relative to hypodermic tube 230, e.g., a static friction force between fixation mechanism 130 and hypodermic tube 230 may be configured to temporarily fix tip stabilization mechanism 110 in a position relative to hypodermic tube 230. In one or more embodiments, a contact between a portion of fixation mechanism 130 and a portion of hypodermic tube 230 may be configured to temporarily fix tip stabilization mechanism 110 in a position relative to hypodermic tube 230. Illustratively, fixation mechanism 130 may be fixed to both tip stabilization mechanism 110 and hypodermic tube 230 wherein a static friction force between fixation mechanism 130 and hypodermic tube 230 may be configured to temporarily fix tip stabilization mechanism 110 in a position relative to hypodermic tube 230.

Illustratively, a portion of irrigating and aspirating tip 640 may be disposed within hypodermic tube 230, e.g., irrigating and aspirating tip proximal end 642 may be disposed within hypodermic tube distal end 231. In one or more embodiments, a portion of irrigating and aspirating tip 640 may be disposed within hypodermic tube 230 wherein a portion of irrigating and aspirating tip 640 extends from a portion of hypodermic tube 230, e.g., a portion of irrigating and aspirating tip 640 may be disposed within hypodermic tube 230 wherein irrigating and aspirating tip distal end 641 extends from hypodermic tube distal end 231. Illustratively, a portion of irrigating and aspirating tip 640 may be fixed within hypodermic tube 230, e.g., irrigating and aspirating tip proximal end 642 may be fixed within hypodermic tube 230. In one or more embodiments, a portion of irrigating and aspirating tip 640 may be fixed within hypodermic tube 230 by an adhesive or any suitable fixation means, e.g., a portion of irrigating and aspirating tip 640 may be fixed within hypodermic tube 230 by a friction fit, a weld, etc.

Illustratively, pressure vent tactile locater 620 may be disposed over a portion of flow control mechanism 610, e.g., pressure vent tactile locater 620 may be disposed over pressure vent 615. In one or more embodiments, pressure vent tactile locater 620 may be fixed to a portion of flow control mechanism 610 by an adhesive or any suitable fixation means. Illustratively, pressure vent tactile locater 620 may be configured to allow a surgeon to tactilely identify a location of pressure vent 615 where visual identification of a location of pressure vent 615 is impractical, e.g., in a dark operating room. In one or more embodiments, pressure vent tactile locater 620 may be configured to indicate one or more properties of assembled irrigating and aspirating instrument 700 to a surgeon, a nurse, or a surgical technician, e.g., pressure vent tactile locater 620 may comprise a color or a marking configured to visually indicate a minimum cannula gauge size that hypodermic tube 230 may ingress to perform a surgical procedure. Illustratively, pressure vent tactile locater 620 may be manufactured from any suitable material, e.g., polymers, metals, metal alloys, etc., or from any combination of suitable materials.

FIG. 7B illustrates a cross-sectional view of an assembled irrigating and aspirating instrument 700. Illustratively, assembled irrigating and aspirating instrument 700 may comprise a fluid chamber 710, a fluid conduit 720, an irrigation taper 730, and a hypodermic tube housing 740. In one or more embodiments, a portion of fluid guide 630 may be disposed within flow control mechanism 610, e.g., fluid guide proximal end 632 may be disposed within flow control mechanism 610. Illustratively, a portion of fluid guide 630 may be fixed within a flow control mechanism 610 by any suitable fixation mechanism, e.g., a portion of fluid guide 630 may be fixed within flow control mechanism 610 by an adhesive, a friction fit, a locking fit, a weld, etc. In one or more embodiments a portion of hypodermic tube 230 may be disposed within a portion of fluid guide 630, e.g., hypodermic tube proximal end 232 may be disposed within hypodermic tube housing 740. Illustratively, a portion of hypodermic tube 230 may be fixed within hypodermic tube housing 740 by any suitable fixation mechanism, e.g., a portion of hypodermic tube 230 may be fixed within hypodermic tube housing 740 by a press-fit, an adhesive, a weld, etc.

Illustratively, irrigating and aspirating tip 640 may be disposed within hypodermic tube 230 and tip stabilization mechanism 110, e.g., irrigating and aspirating tip distal end 641 may be disposed between tip stabilization mechanism distal end 111 and tip stabilization mechanism proximal end 112. In one or more embodiments, irrigating and aspirating tip 640 may be disposed within hypodermic tube 230 and tip stabilization mechanism 110 wherein irrigating and aspirating tip proximal end 642 may be disposed between hypodermic tube distal end 231 and hypodermic tube proximal end 232. Illustratively, hypodermic tube 230 may be disposed within tip stabilization mechanism 110 wherein hypodermic tube distal end 231 is disposed between tip stabilization mechanism distal end 111 and tip stabilization mechanism proximal end 112.

Figure 8:
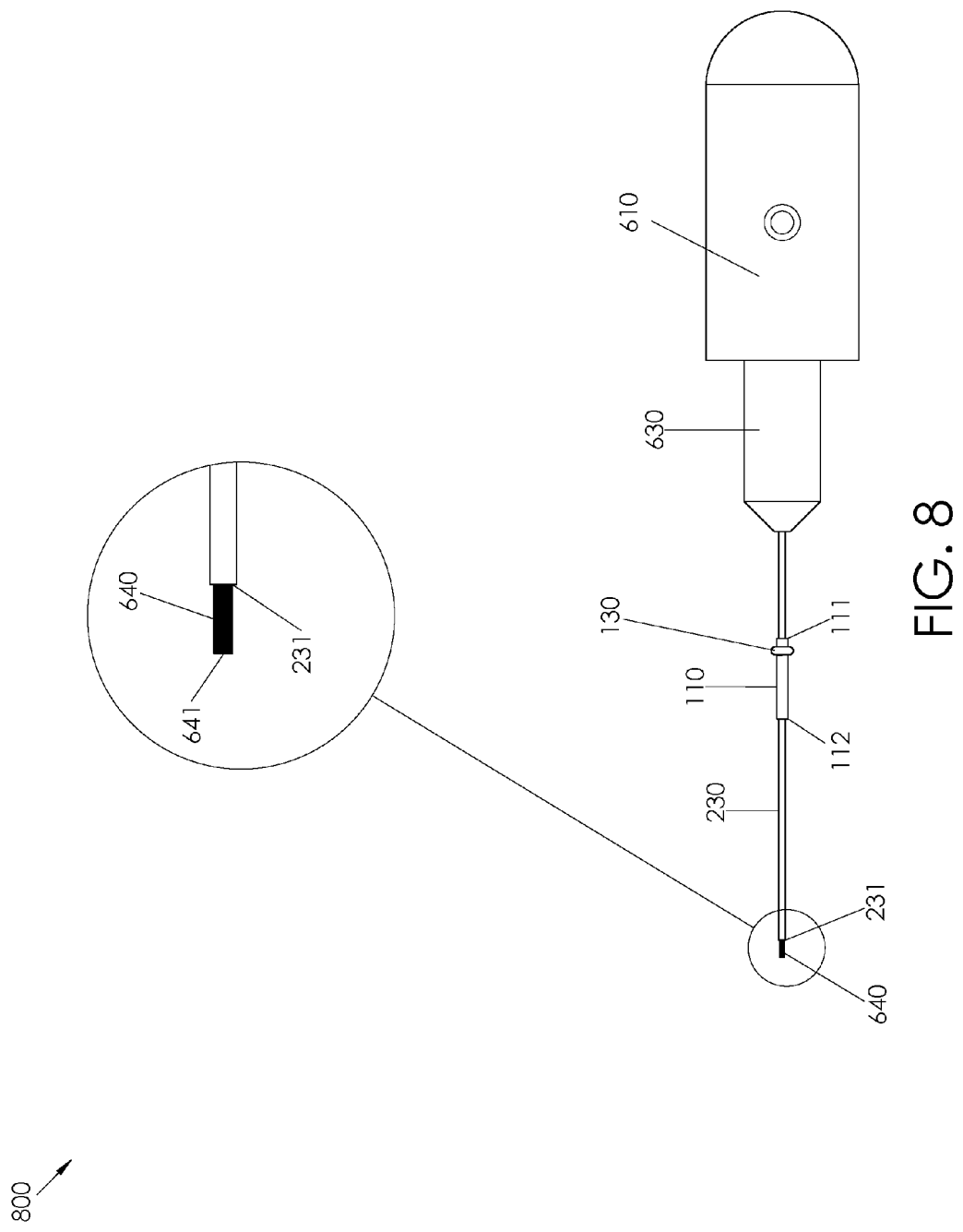
FIG. 8 is a schematic diagram illustrating an exposed irrigating and aspirating tip.

FIG. 8 is a schematic diagram illustrating an exposed irrigating and aspirating tip 800. In one or more embodiments, irrigating and aspirating tip 640 may be colored black, e.g., to enhance visualization of irrigating and aspirating tip 640. For example, irrigating and aspirating tip 640 may be manufactured from black silicone to enhance visualization of irrigating and aspirating tip 640. Illustratively, irrigating and aspirating tip 640 may be colored any color not contained within Johannes Itten's color wheel to enhance visualization of irrigating and aspirating tip 640, e.g., irrigating and aspirating tip 640 may be colored black or grey to enhance visualization of irrigating and aspirating tip 640. In one or more embodiments, irrigating and aspirating tip 640 may be configured to irrigate fluid into inner eye 565. Illustratively, irrigating and aspirating tip 640 may be configured to aspirate fluid out from inner eye 565. In one or more embodiments, irrigating and aspirating tip 640 may be configured to both irrigate fluid into inner eye 565 and to aspirate fluid out from inner eye 565.

Figure 9A:
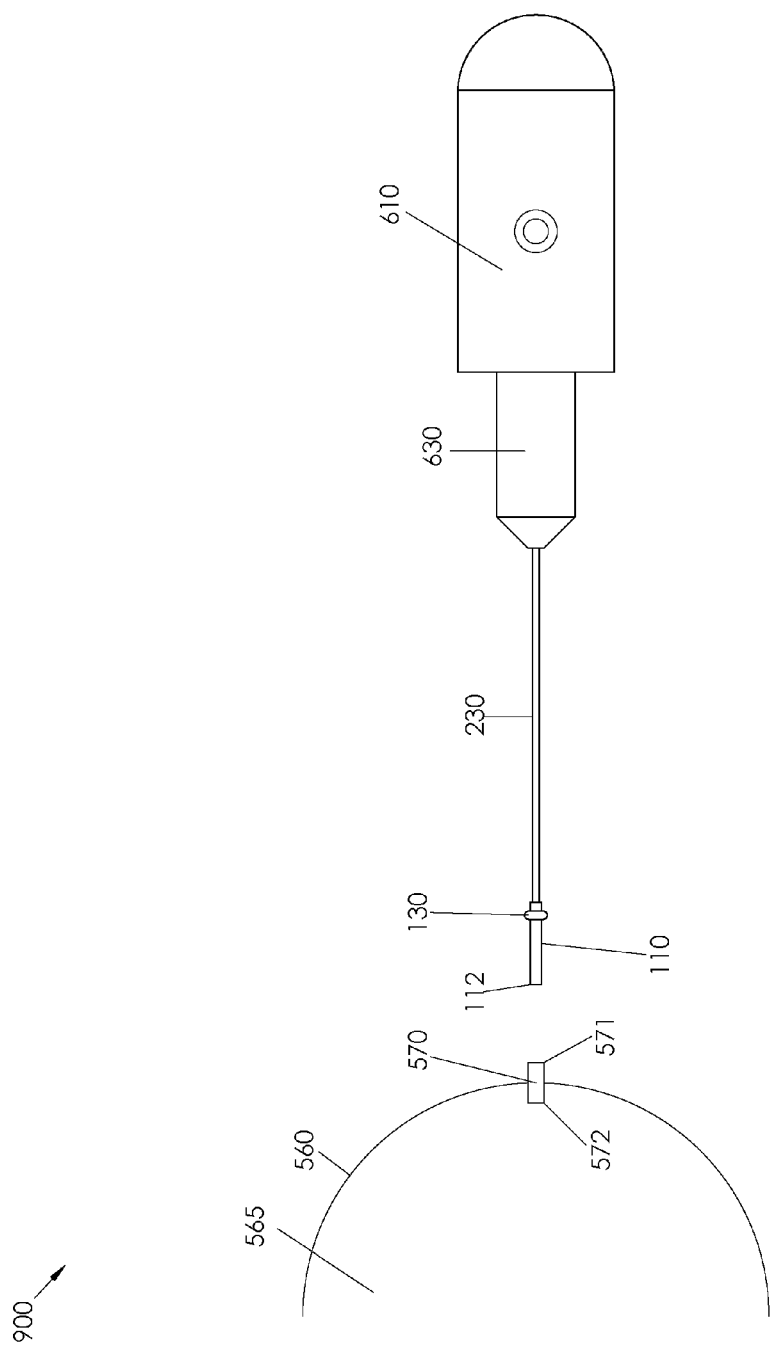
FIGS. 9A, 9B, 9C, 9D, 9E, and 9F are schematic diagrams illustrating a portion of a surgical procedure.

FIGS. 9A, 9B, 9C, 9D, 9E, and 9F are schematic diagrams illustrating a portion of a surgical procedure. FIG. 9A illustrates a cannula approach 900. Illustratively, a surgeon may maneuver an assembled irrigating and aspirating instrument 700 towards an eye 560 to perform a portion of a surgical procedure, e.g., a surgeon may maneuver an assembled irrigating and aspirating instrument 700 towards a cannula 570 to perform a portion of a surgical procedure. In one or more embodiments, cannula 570 may comprise a cannula distal end 571 and a cannula proximal end 572. Illustratively, cannula 570 may be disposed within an incision in eye 560, e.g., cannula 570 may be disposed within an incision in eye 560 wherein cannula distal end 571 extends out from an outer surface of eye 560 and cannula proximal end 572 is disposed within an inner eye 565. In one or more embodiments, a cannula approach 900 may comprise an attempt to guide tip stabilization mechanism proximal end 112 towards cannula distal end 571.

Figure 9B:
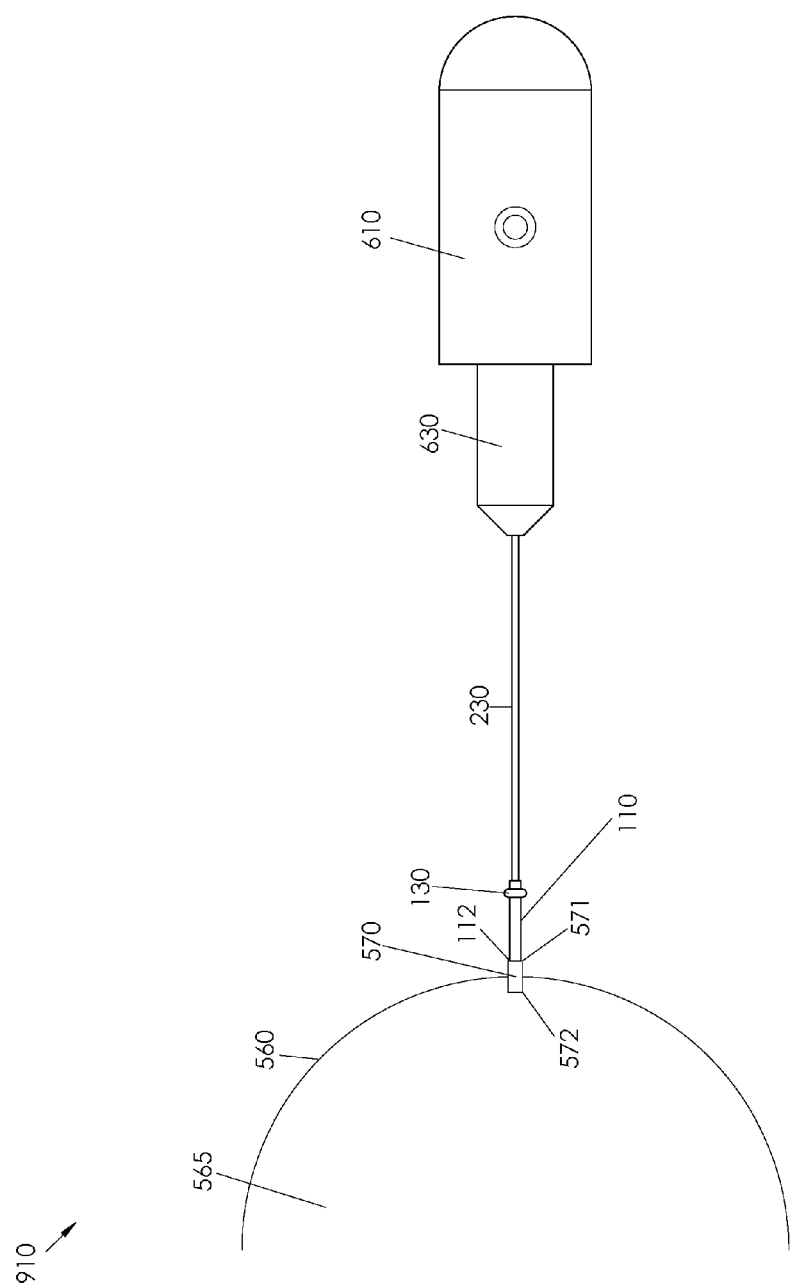

FIG. 9B illustrates a cannula contact 910. Illustratively, a surgeon may approach cannula 570 with assembled irrigating and aspirating instrument 700 until a portion of assembled irrigating and aspirating instrument 700 contacts a portion of cannula 570, e.g., a surgeon may approach cannula 570 with assembled irrigating and aspirating instrument 700 until tip stabilization mechanism proximal end 112 contacts cannula distal end 571. In one or more embodiments, a cannula contact 510 may comprise a contact between tip stabilization mechanism proximal end 112 and cannula distal end 571. Illustratively, a cannula contact 510 may be configured to apply a force to fixation mechanism 130, e.g., a cannula contact 510 may apply a normal force to tip stabilization mechanism 110. In one or more embodiments, an application of a normal force to tip stabilization mechanism 110 may be configured to retract tip stabilization mechanism 110 relative to hypodermic tube 230, e.g., a normal force applied to tip stabilization mechanism 110 may be greater than a static friction force between fixation mechanism 130 and hypodermic tube 230. Illustratively, an application of a normal force to tip stabilization mechanism 110 may not be configured to retract tip stabilization mechanism 110 relative to hypodermic tube 230, e.g., a normal force applied to tip stabilization mechanism 110 may be less than a static friction force between fixation mechanism 130 and hypodermic tube 230.

Figure 9C:
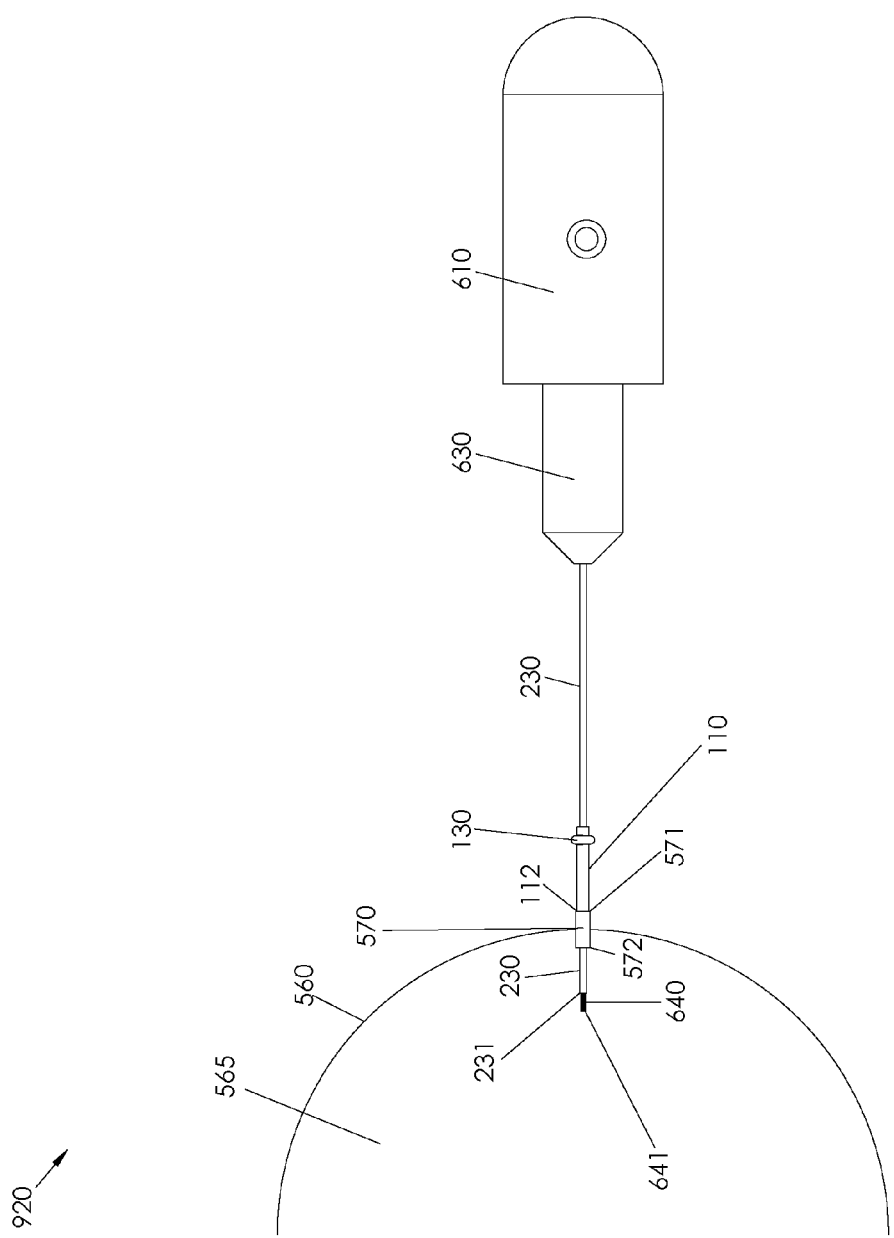

FIG. 9C illustrates a partial irrigating and aspirating tip insertion 920. Illustratively, a surgeon may guide a portion of assembled irrigating and aspirating instrument 700 into cannula 570, e.g., by advancing flow control mechanism 610 towards eye 560 after a cannula contact 510. In one or more embodiments, advancing flow control mechanism 610 towards eye 560 after a cannula contact 510 may be configured to apply a force to tip stabilization mechanism proximal end 112. Illustratively, an application of a force to tip stabilization mechanism proximal end 112 may be configured to actuate tip stabilization mechanism 110 relative to hypodermic tube 230, e.g., an application of a force to tip stabilization mechanism proximal end 112 may be configured to actuate tip stabilization mechanism distal end 111 towards handle distal end 211. In one or more embodiments, advancing flow control mechanism 610 towards eye 560 after a cannula contact 510 may be configured to apply a force to tip stabilization mechanism 110 that is greater than a static friction force between fixation mechanism 130 and hypodermic tube 230. Illustratively, advancing flow control mechanism 610 towards eye 560 after a cannula contact 510 may be configured to retract tip stabilization mechanism 110 and fixation mechanism 130 relative to hypodermic tube 230. In one or more embodiments, advancing flow control mechanism 610 towards eye 560 after a cannula contact 510 may actuate irrigating and aspirating tip distal end 641 into cannula distal end 571. Illustratively, advancing flow control mechanism 610 towards eye 560 after a cannula contact 510 may be configured to actuate hypodermic tube distal end 231 into cannula distal end 571. In one or more embodiments, advancing flow control mechanism 610 towards eye 560 after a cannula contact 510 may be configured to actuate irrigating and aspirating tip distal end 641 out from cannula proximal end 572. Illustratively, advancing flow control mechanism 610 towards eye 560 after a cannula contact 510 may be configured to actuate hypodermic tube distal end 231 out from cannula proximal end 572. In one or more embodiments, advancing flow control mechanism 610 towards eye 560 after a cannula contact 510 may be configured to actuate irrigating and aspirating tip 640 into inner eye 565.

Figure 9D:
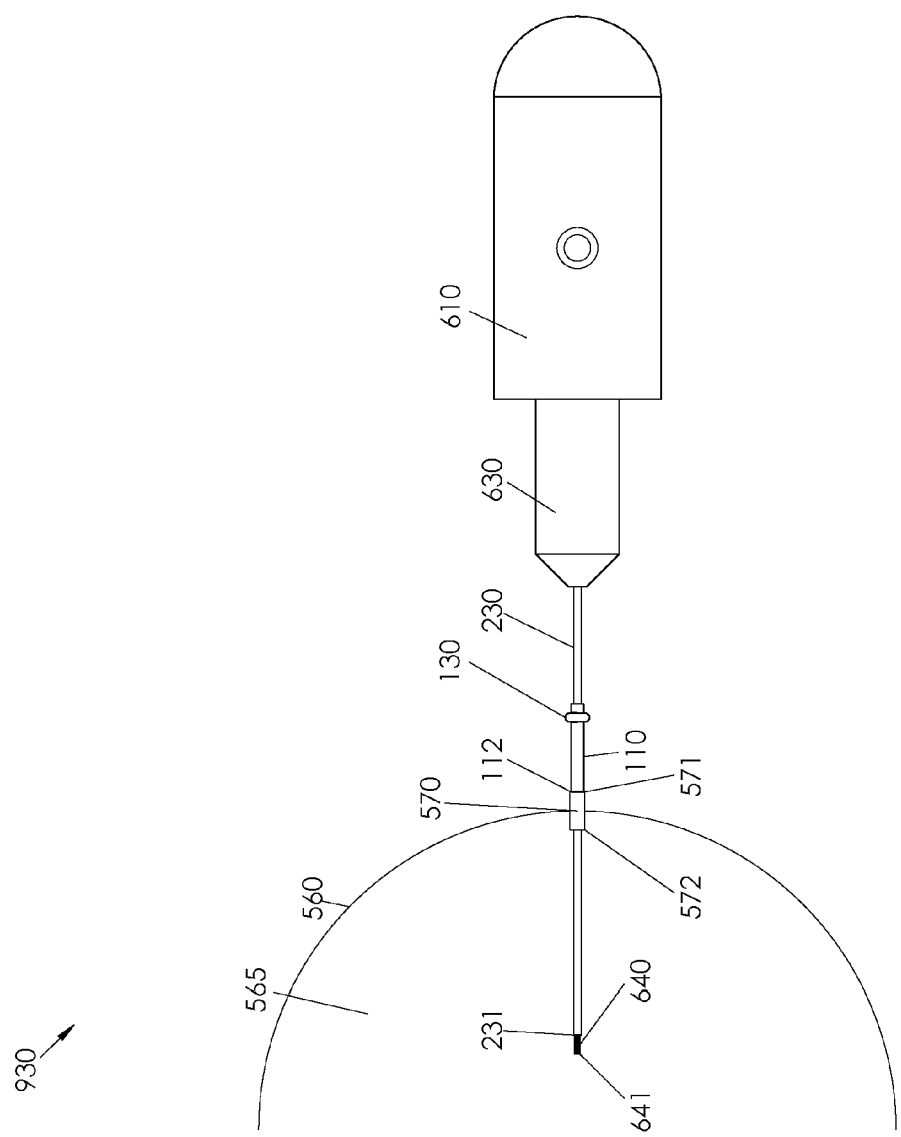

FIG. 9D illustrates a complete irrigating and aspirating tip insertion 930. In one or more embodiments, advancing flow control mechanism 610 towards eye 560 after a partial irrigating and aspirating tip insertion 920 may be configured to apply a force to tip stabilization mechanism proximal end 112. Illustratively, an application of a force to tip stabilization mechanism proximal end 112 may be configured to actuate tip stabilization mechanism 110 relative to hypodermic tube 230, e.g., an application of a force to tip stabilization mechanism proximal end 112 may be configured to actuate tip stabilization mechanism distal end 111 towards fluid guide distal end 631. In one or more embodiments, advancing flow control mechanism 610 towards eye 560 after a partial irrigating and aspirating tip insertion 920 may be configured to apply a force to tip stabilization mechanism 110 that is greater than a static friction force between fixation mechanism 130 and hypodermic tube 230. Illustratively, advancing flow control mechanism 610 towards eye 560 after a partial irrigating and aspirating tip insertion 920 may be configured to retract tip stabilization mechanism 110 and fixation mechanism 130 relative to hypodermic tube 230. In one or more embodiments, advancing flow control mechanism 610 towards eye 560 after a partial irrigating and aspirating tip insertion 920 may be configured to actuate irrigating and aspirating tip 640 within inner eye 565.

Figure 9E:
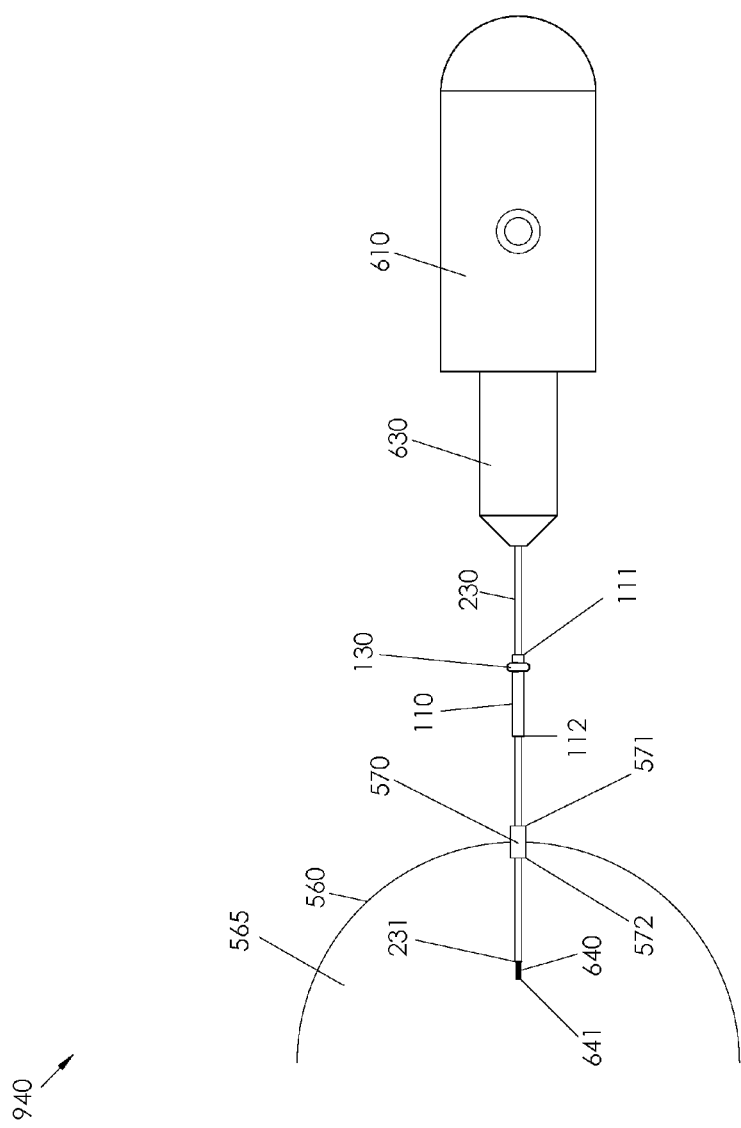

FIG. 9E illustrates a partial irrigating and aspirating tip extraction 940. Illustratively, a surgeon may guide a portion of assembled irrigating and aspirating instrument 700 out from cannula 570, e.g., by retracting flow control mechanism 610 away from eye 560 after a complete irrigating and aspirating tip insertion 930. In one or more embodiments, retracting flow control mechanism 610 away from eye 560 may be configured to reduce a force applied to tip stabilization mechanism 110. Illustratively, reducing a force applied to tip stabilization mechanism 110 may be configured to fix tip stabilization mechanism 110 and fixation mechanism 130 in a position relative to hypodermic tube 230. In one or more embodiments, a surgeon may use a distance between tip stabilization mechanism proximal end 112 and cannula distal end 571 as a depth gauge to evaluate a risk associated with a surgical procedure, e.g., during a difficult membrane removal, a surgeon may be concerned about damaging a patient's retinal tissue. Illustratively, a surgeon may use a distance between tip stabilization mechanism proximal end 112 and cannula distal end 571 as a depth gauge to compare a depth into the posterior segment of inner eye 565 of a particular portion of a surgical procedure with a depth into the posterior segment of inner eye 565 of a prior portion of a surgical procedure.

Figure 9F:
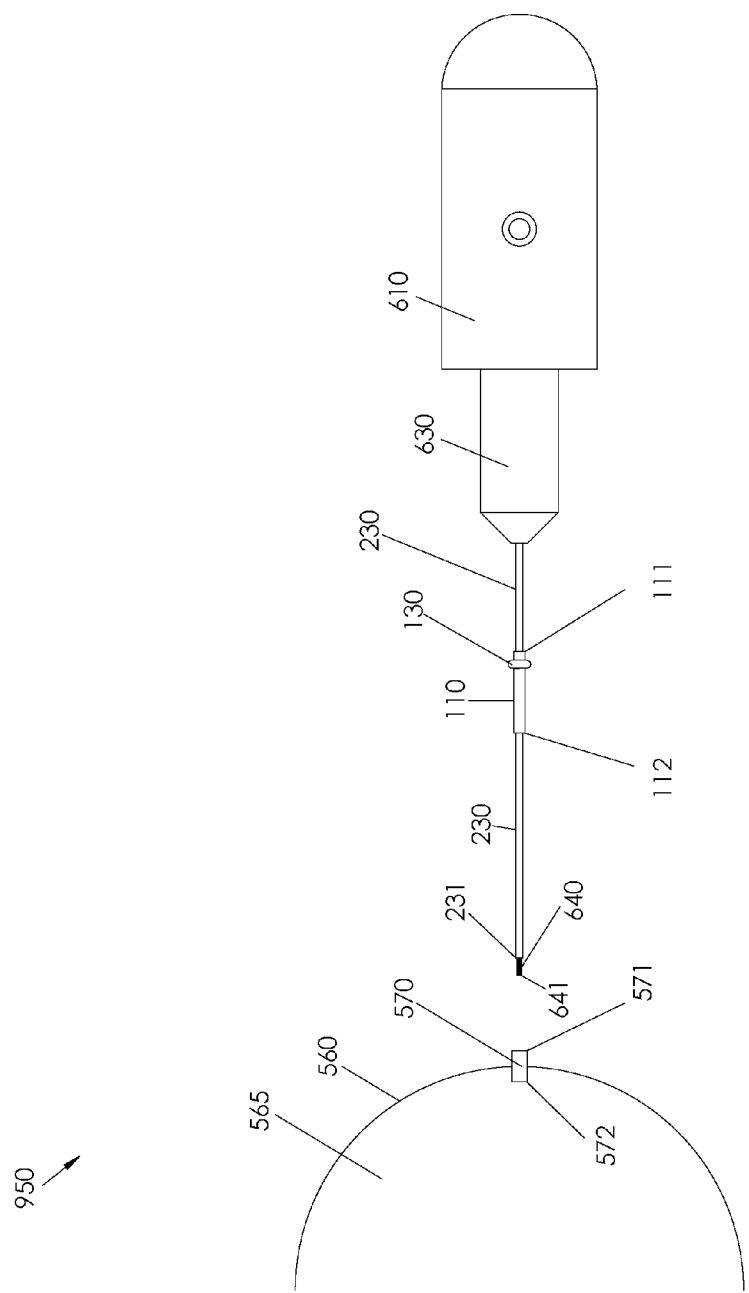

FIG. 9F illustrates a complete irrigating and aspirating tip extraction 950. Illustratively, a surgeon may guide a portion of assembled irrigating and aspirating instrument 700 out from cannula 570, e.g., by retracting flow control mechanism 610 away from eye 560 after a partial irrigating and aspirating tip extraction 940. In one or more embodiments, retracting flow control mechanism 610 away from eye 560 after a partial irrigating and aspirating tip extraction 940 may be configured to extract irrigating and aspirating tip 610 from cannula 570. Illustratively, after a complete irrigating and aspirating tip extraction 950, tip stabilization mechanism 110 may be fixed in a position relative to hypodermic tube 230, e.g., assembled irrigating and aspirating instrument 700 may comprise an exposed irrigating and aspirating tip 800 after a complete irrigating and aspirating tip extraction 950. In one or more embodiments, a surgeon may prepare assembled irrigating and aspirating instrument 700 for a second cannula approach 900 after a complete irrigating and aspirating tip extraction 950 by grasping tip stabilization mechanism 110 and actuating tip stabilization mechanism 110 relative to hypodermic tube 230 towards irrigating and aspirating tip 640. Illustratively, a surgeon may prepare assembled irrigating and aspirating instrument 700 for a second cannula approach 900 after a complete irrigating and aspirating tip extraction 950 by actuating tip stabilization mechanism 110 over irrigating and aspirating tip 640.

FIGS. 10A, 10B, 10C, 10D, and 10E are schematic diagrams illustrating a portion of a surgical procedure. FIG.

10A illustrates a valved cannula approach 1000. Illustratively, a valved cannula 1050 may comprise an inner lumen 1055, a first valve hinge 1065, a second valve hinge 1065, and a valve hinge interface 1060. In one or more embodiments, first valve hinge 1065 may comprise a first valve hinge superior surface 1066 and second valve hinge 1065 may comprise a second valve hinge superior surface 1066. Illustratively, valved cannula 1050 may be configured to maintain an intraocular pressure, e.g., valve hinge interface 1060 may be configured to maintain an intraocular pressure during a surgical procedure. In one or more embodiments, a surgeon may guide tip stabilization mechanism 110 towards valved cannula 1050 to perform a portion of a surgical procedure, e.g., a surgeon may guide tip stabilization mechanism proximal end 112 towards valve hinge superior surface 1066 to perform a portion of a surgical procedure. Illustratively, as a surgeon guides tip stabilization mechanism proximal end 112 towards valve hinge superior surface 1066, hypodermic tube distal end 231 may be disposed within tip stabilization mechanism inner bore 120. In one or more embodiments, as a surgeon guides tip stabilization mechanism proximal end 112 towards valve hinge superior surface 1066, membrane removing tip distal end 241 may be disposed within tip stabilization mechanism inner bore 120.

Figure 10A:
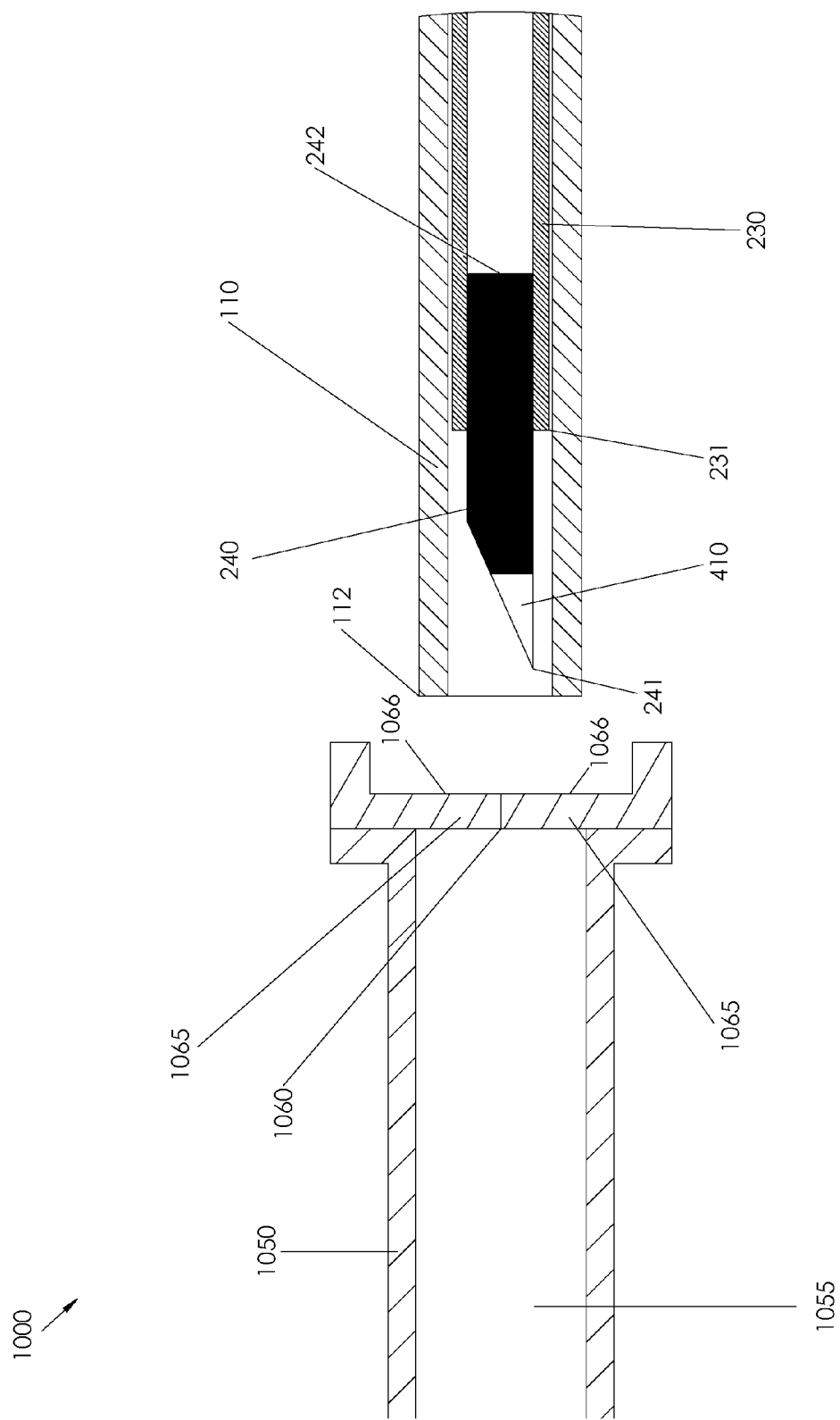
FIGS. 10A, 10B, 10C, 10D, and 10E are schematic diagrams illustrating a portion of a surgical procedure.
Figure 10B:
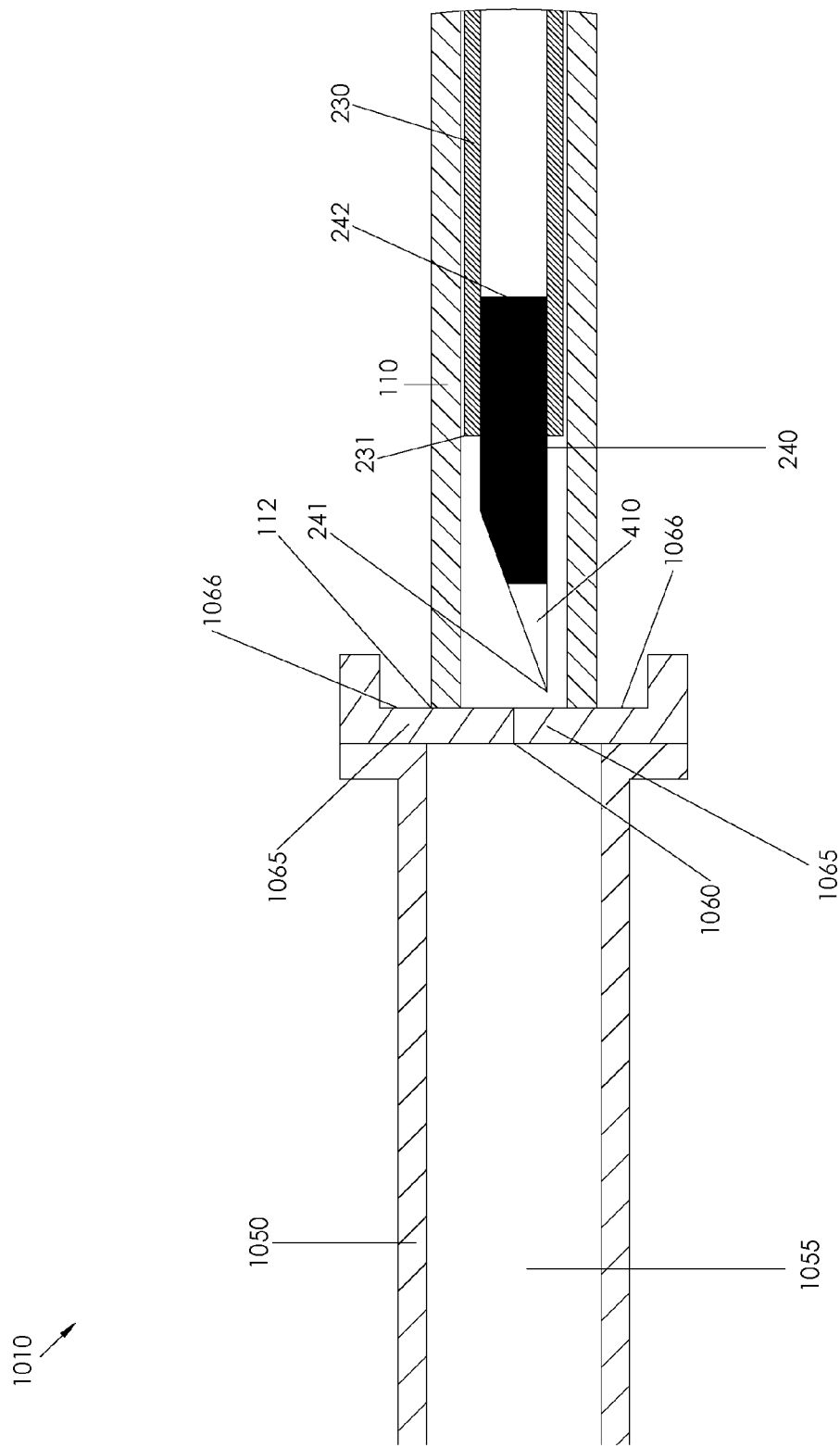

FIG. 10B illustrates a valved cannula contact 1010. In one or more embodiments, a valved cannula contact 1010 may comprise a contact between a portion of tip stabilization mechanism 110 and a portion of valved cannula 1050, e.g., a valved cannula contact 1010 may comprise a contact between tip stabilization mechanism proximal end 112 and valve hinge superior surface 1066. Illustratively, a valved cannula contact 1010 may be configured to apply a force to fixation mechanism 130, e.g., a valved cannula contact 1010 may apply a normal force to tip stabilization mechanism 110. In one or more embodiments, an application of a normal force to tip stabilization mechanism 110 may be configured to retract tip stabilization mechanism 110 relative to hypodermic tube 230, e.g., a normal force applied to tip stabilization mechanism 110 may be greater than a static friction force between fixation mechanism 130 and hypodermic tube 230. Illustratively, an application of a normal force to tip stabilization mechanism 110 may not be configured to retract tip stabilization mechanism 110 relative to hypodermic tube 230, e.g., a normal force applied to tip stabilization mechanism 110 may be less than a static friction force between fixation mechanism 130 and hypodermic tube 230.

Figure 10C:
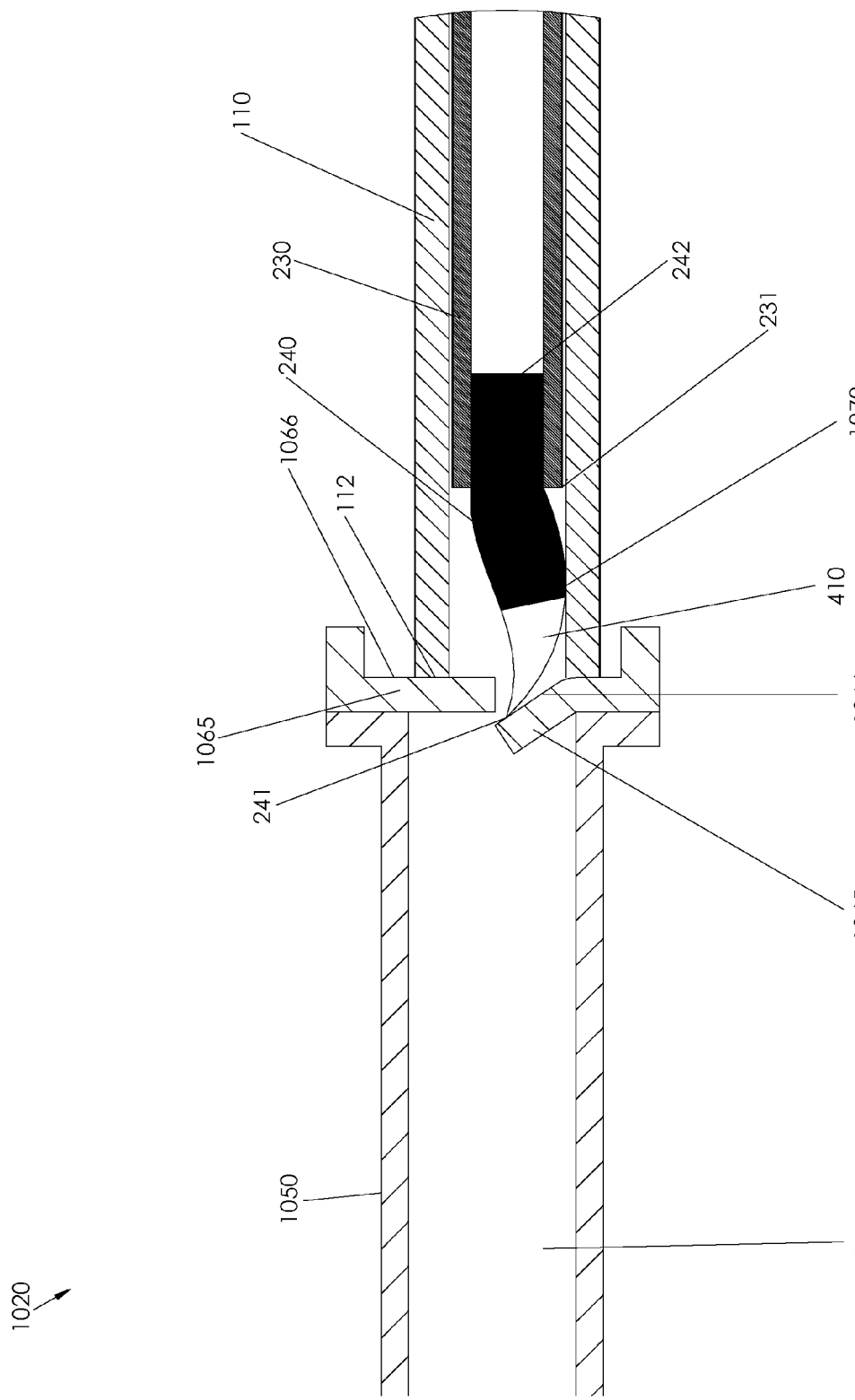

FIG. 10C illustrates a membrane removing tip stabilization 1020. Illustratively, a surgeon may actuate hypodermic tube 230 towards inner lumen 1055 after a valved cannula contact 1010, e.g., a surgeon may actuate hypodermic tube distal end 231 towards inner lumen 1055 after a valved cannula contact 1010. In one or more embodiments, actuating hypodermic tube 230 towards inner lumen 1055 after a valved cannula contact 1010 may be configured to apply a force to tip stabilization mechanism 110, e.g., actuating hypodermic tube distal end 231 towards inner lumen 1055 after a valved cannula contact 1010 may be configured to apply a force to tip stabilization mechanism proximal end 112. Illustratively, an application of a force to tip stabilization mechanism 110 may be configured to actuate tip stabilization mechanism 110 relative to housing tube 230, e.g., an application of a force to tip stabilization mechanism proximal end 112 that is greater than a force of static friction between fixation mechanism 130 and hypodermic tube 230 may be configured to retract tip stabilization mechanism 110 relative to hypodermic tube 230. Illustratively, an application of a force to tip stabilization mechanism proximal end 112 may be configured to actuate tip stabilization mechanism distal end 111 towards hypodermic tube proximal end 232. In one or more embodiments, an actuation of tip stabilization mechanism 110 relative to housing tube 230 may be configured to expose a portion of membrane removing tip 240, e.g., an actuation of tip stabilization mechanism distal end 111 towards hypodermic tube proximal end 232 may be configured to expose membrane removing tip distal end 241. Illustratively, an exposure of a portion of membrane removing tip 240 may be configured to facilitate a contact between membrane removing tip 240 and valve hinge superior surface 1066, e.g., an exposure of a portion of membrane removing tip 240 may be configured to facilitate a contact between membrane removing tip distal end 241 and valve hinge superior surface 1066. In one or more embodiments, as a surgeon actuates hypodermic tube distal end 231 towards inner lumen 1055, a contact between membrane removing tip 240 and valve hinge superior surface 1066 may be configured to cause membrane removing tip 240 to deform, e.g., a contact between membrane removing tip 240 and valve hinge superior surface 1066 may be configured to cause membrane removing tip 240 to bend or flex. Illustratively, a contact between membrane removing tip 240 and valve hinge superior surface 1066 may be configured to cause an elastic deformation of membrane removing tip 240. In one or more embodiments, a contact between membrane removing tip 240 and valve hinge superior surface 1066 may be configured to cause a plastic deformation of membrane removing tip 240.

Illustratively, tip stabilization mechanism 110 may be configured to facilitate a membrane removing tip deformation prevention 1070, e.g., tip stabilization mechanism inner diameter 114 may be configured to prevent membrane removing tip 240 from deforming. In one or more embodiments, tip stabilization mechanism 110 may be configured to prevent a portion of membrane removing tip 240 from deforming beyond a line tangent to a wall of inner lumen 1055, e.g., tip stabilization mechanism inner diameter 114 may be configured to prevent a portion of membrane removing tip 240 from deforming beyond a line tangent to a wall of inner lumen 1055. For example, tip stabilization mechanism 110 may be configured to prevent a portion of membrane removing tip 240 from bending or flexing beyond a line tangent to a wall of inner lumen 1055. Illustratively, tip stabilization mechanism 110 may be configured to prevent a portion of membrane removing tip 240 from deforming beyond a line tangent to an outer diameter of valved cannula 1050, e.g., tip stabilization mechanism inner diameter 114 may be configured to prevent a portion of membrane removing tip 240 from deforming beyond a line tangent to an outer diameter of valved cannula 1050. For example, tip stabilization mechanism 110 may be configured to prevent a portion of membrane removing tip 240 from bending or flexing beyond a line tangent to an outer diameter of valved cannula 1050. In one or more embodiments, a membrane removing tip deformation prevention 1070 may be configured to actuate valve hinge 1065, e.g., a membrane removing tip deformation prevention 1070 may be configured to separate a first valve hinge 1065 and a second valve hinge 1065 at valve hinge interface 1060. Illustratively, a membrane removing tip deformation prevention 1070 may be configured to guide a portion of membrane removing tip 240 into inner lumen 1055, e.g., a membrane removing tip deformation prevention 1070 may be configured to guide membrane removing tip distal end 241 into inner lumen 1055. In one or more embodiments, membrane removing tip 240 may have a first stiffness, valve hinge 1065 may have a second stiffness, and tip stabilization mechanism 110 may have a third stiffness wherein the second stiffness is greater than the first stiffness and the third stiffness is greater than the second stiffness. Illustratively, the second stiffness of valve hinge 1065 may be configured to cause a deformation of membrane removing tip 240 and the third stiffness of tip stabilization mechanism 110 may be configured to guide a portion of membrane removing tip 240 into inner lumen 1055.

Figure 10D:
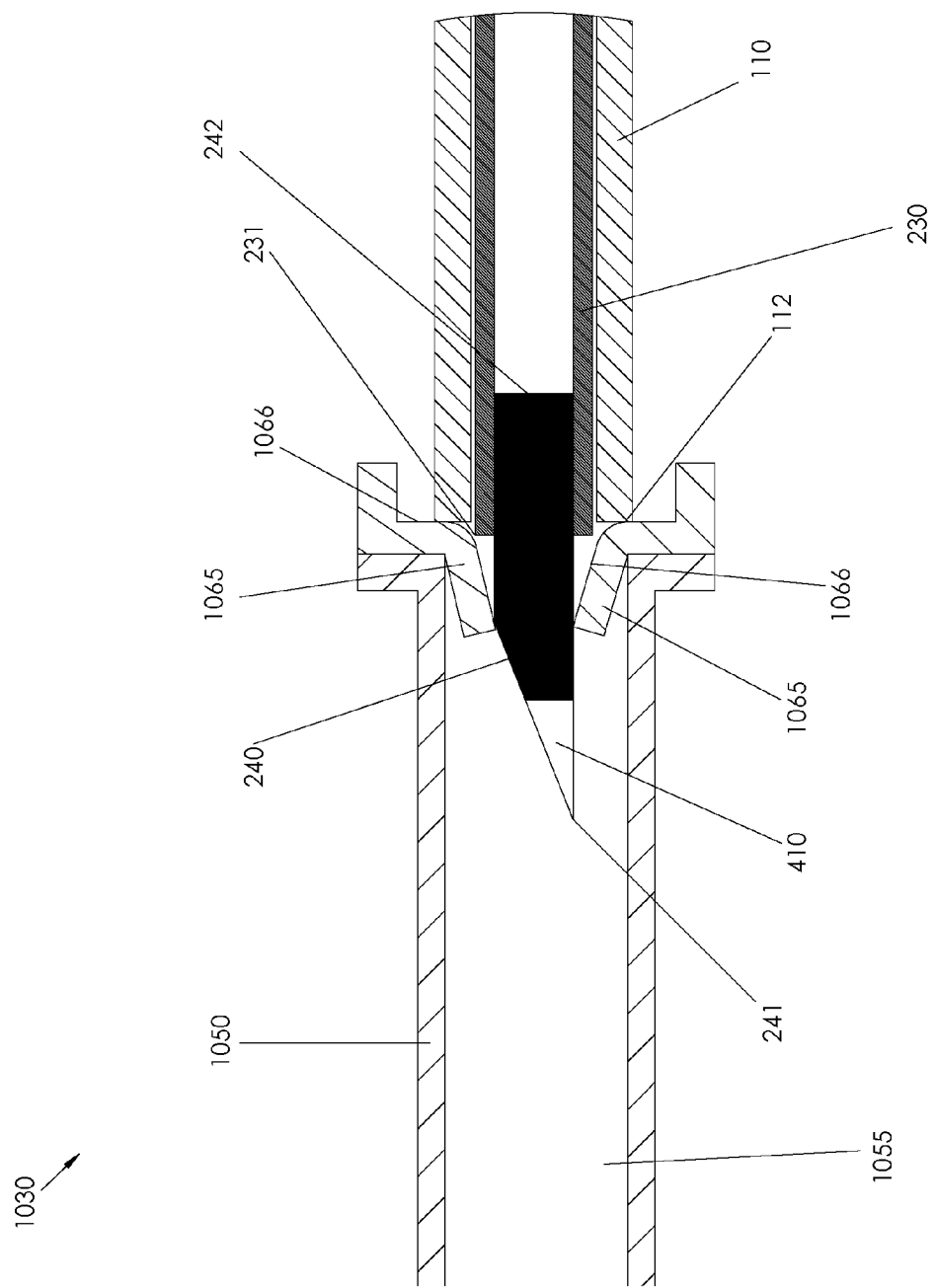

FIG. 10D illustrates a partial valved cannula ingress 1030. Illustratively, a surgeon may actuate hypodermic tube 230 towards inner lumen 1055 after a membrane removing tip stabilization 1020, e.g., a surgeon may actuate hypodermic tube distal end 231 towards inner lumen 1055 after a membrane removing tip stabilization 1020. In one or more embodiments, an actuation of hypodermic tube distal end 231 towards inner lumen 1055 after a membrane removing tip stabilization 1020 may be configured to actuate a portion of membrane removing tip 240 into valved cannula 1050, e.g., an actuation of hypodermic tube distal end 231 towards inner lumen 1055 after a membrane removing tip stabilization 1020 may be configured to actuate membrane removing tip distal end 241 into inner lumen 1055. Illustratively, an actuation of hypodermic tube distal end 231 towards inner lumen 1055 after a membrane removing tip stabilization 1020 may be configured to actuate abrasive surface 410 into inner lumen 1055. In one or more embodiments, an actuation of hypodermic tube distal end 231 towards inner lumen 1055 after a membrane removing tip stabilization 1020 may be configured to increase a separation of a first valve hinge 1065 and a second valve hinge 1065. Illustratively, an actuation of hypodermic tube distal end 231 towards inner lumen 1055 after a membrane removing tip stabilization 1020 may be configured to cause membrane removing tip 240 to return to its original geometry, e.g., an actuation of hypodermic tube distal end 231 towards inner lumen 1055 after a membrane removing tip stabilization 1020 may be configured to cause membrane removing tip 240 to return to its pre-deformation geometry.

Figure 10E:
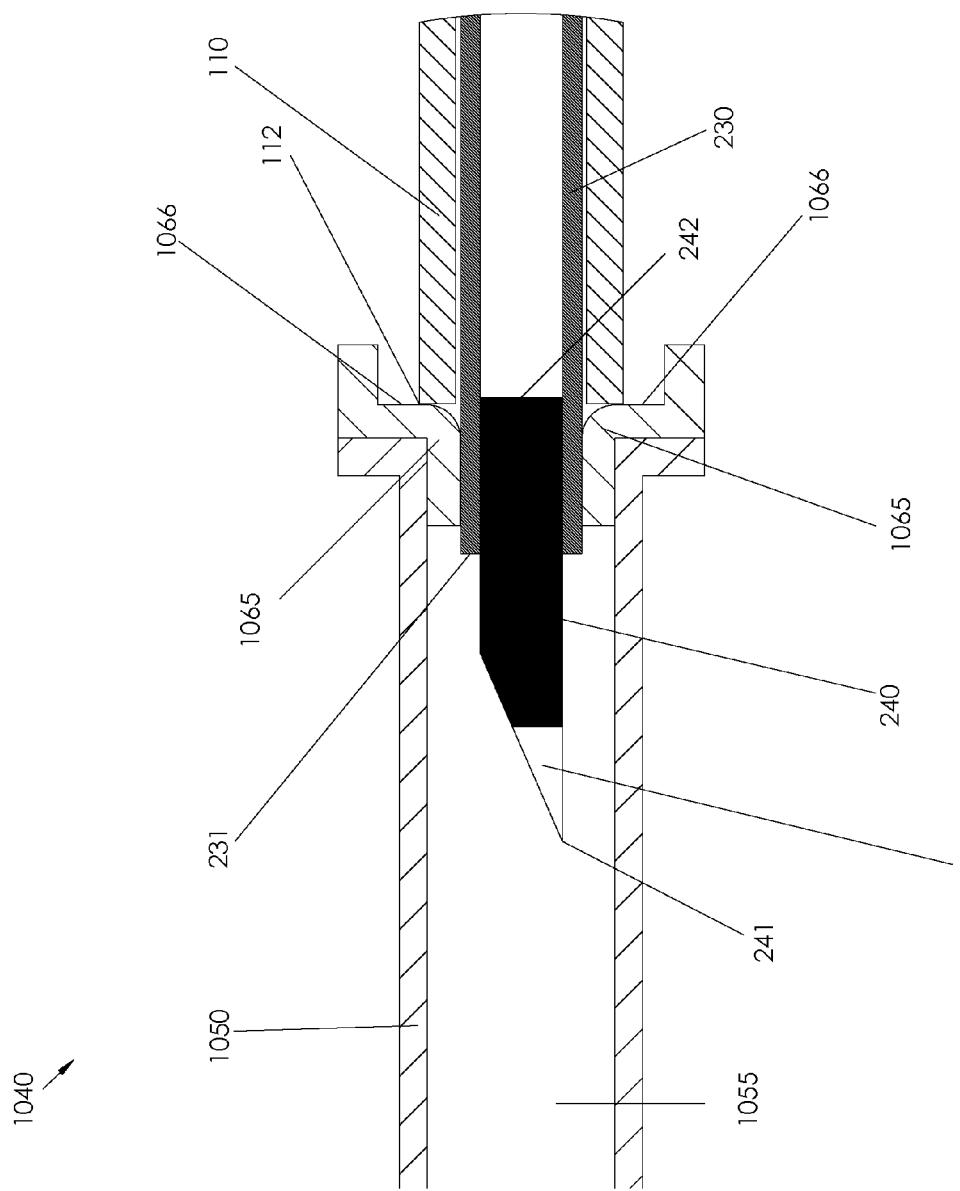

FIG. 10E illustrates a complete valved cannula ingress 1040. Illustratively, a surgeon may actuate hypodermic tube 230 towards inner lumen 1055 after a partial valved cannula ingress 1030, e.g., a surgeon may actuate hypodermic tube distal end 231 into inner lumen 1055 after a partial valved cannula ingress 1030. In one or more embodiments, an actuation of hypodermic tube distal end 231 into inner lumen 1055 after a partial valved cannula ingress 1030 may be configured to fully separate a first valve hinge 1065 and a second valve hinge 1065. Illustratively, an actuation of hypodermic tube distal end 231 into inner lumen 1055 after a partial valved cannula ingress 1030 may be configured to cause a portion of hypodermic tube 230 to contact a portion of valve hinge superior surface 1066, e.g., an actuation of hypodermic tube distal end 231 into inner lumen 1055 after a partial valved cannula ingress 1030 may be configured to cause an outer portion of hypodermic tube 230 to contact a portion of valve hinge superior surface 1066.

Figure 11A:
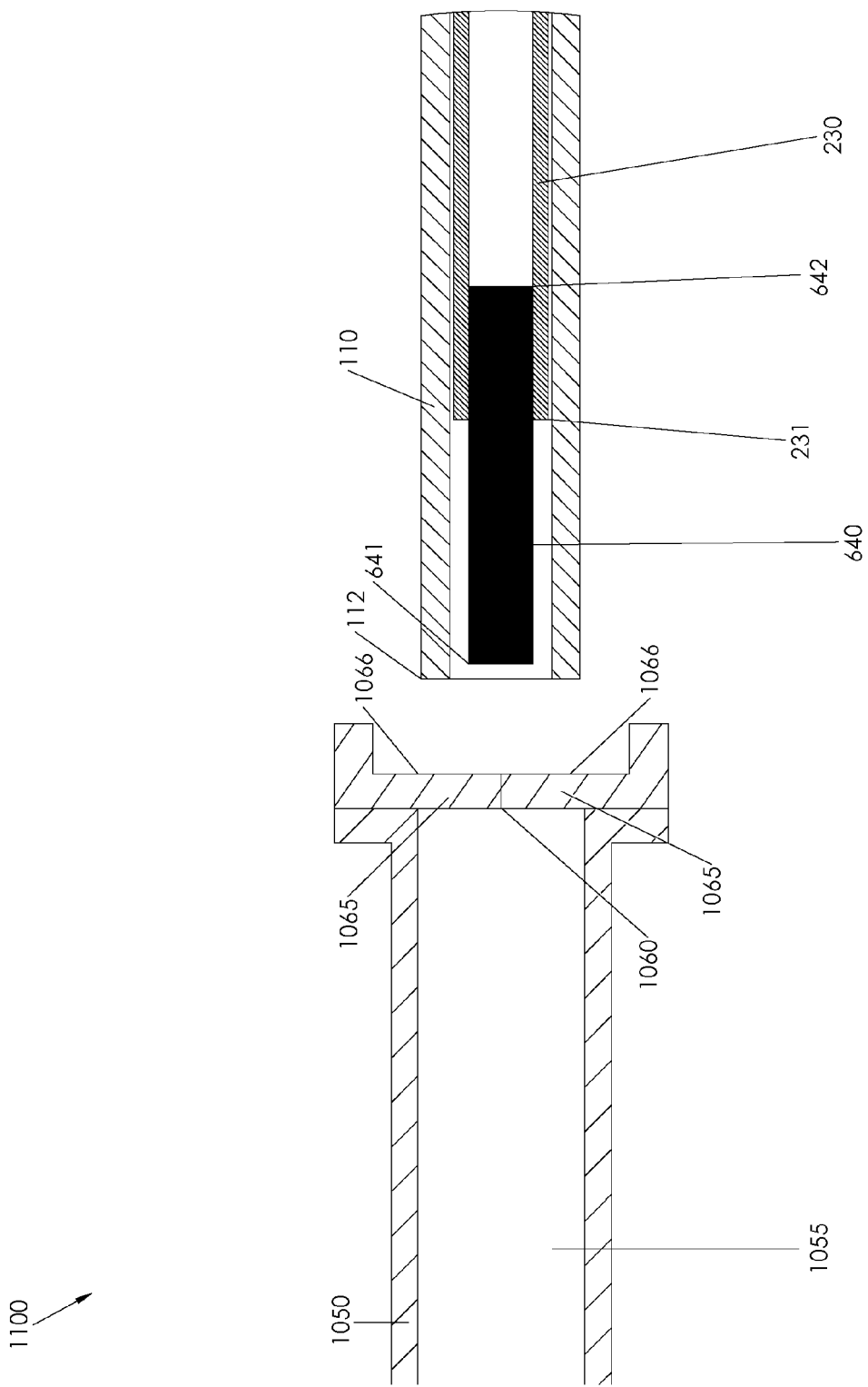
FIGS. 11A, 11B, 11C, 11D, and 11E are schematic diagrams illustrating a portion of a surgical procedure.

FIGS. 11A, 11B, 11C, 11D, and 11E are schematic diagrams illustrating a portion of a surgical procedure. FIG. 11A illustrates a valved cannula approach 1100. In one or more embodiments, a surgeon may guide tip stabilization mechanism 110 towards valved cannula 1050 to perform a portion of a surgical procedure, e.g., a surgeon may guide tip stabilization mechanism proximal end 112 towards valve hinge superior surface 1066 to perform a portion of a surgical procedure. Illustratively, as a surgeon guides tip stabilization mechanism proximal end 112 towards valve hinge superior surface 1066, hypodermic tube distal end 231 may be disposed within tip stabilization mechanism inner bore 120. In one or more embodiments, as a surgeon guides tip stabilization mechanism proximal end 112 towards valve hinge superior surface 1066, irrigating and aspirating tip distal end 641 may be disposed within tip stabilization mechanism inner bore 120.

Figure 11B:
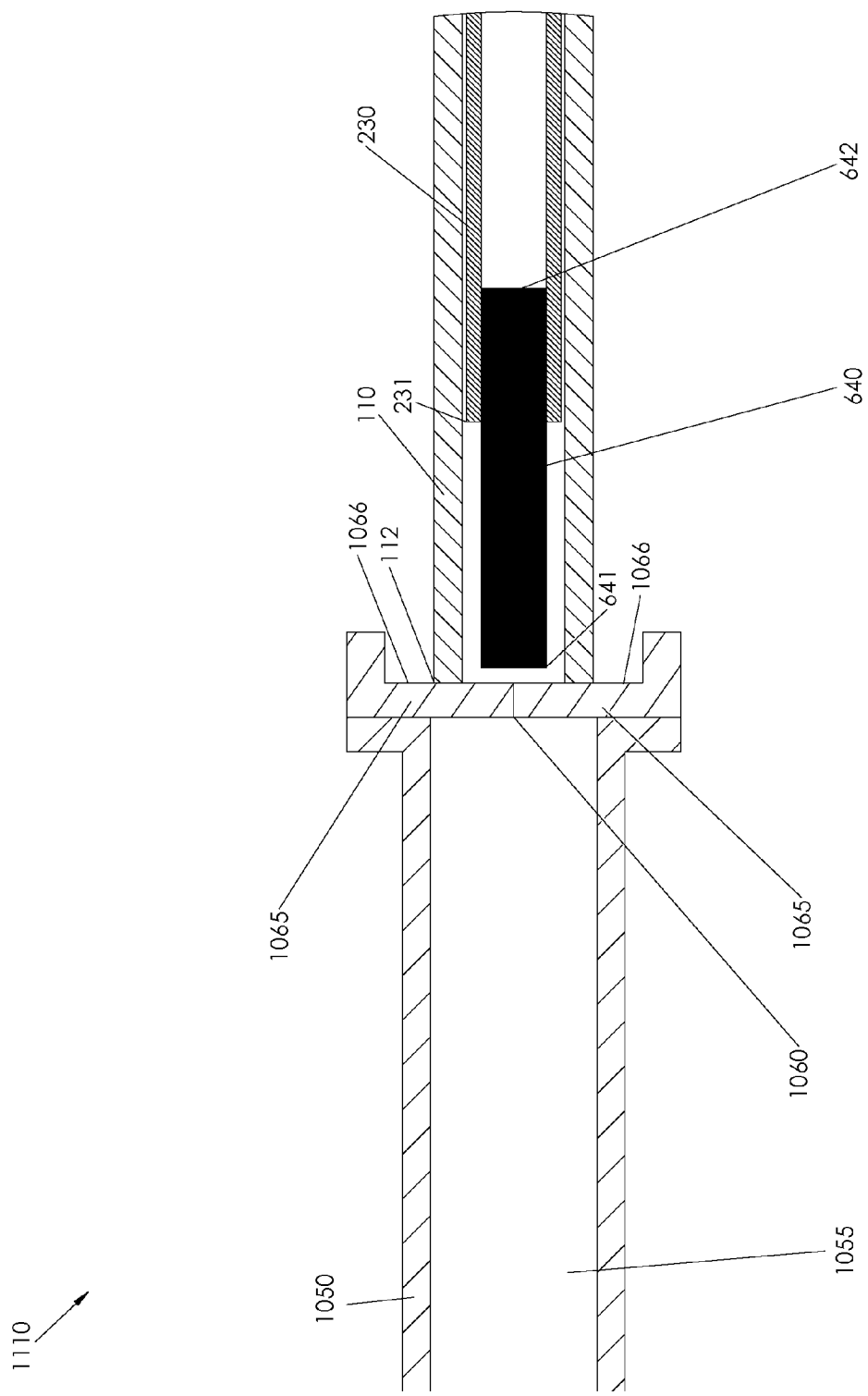

FIG. 11B illustrates a valved cannula contact 1110. In one or more embodiments, a valved cannula contact 1110 may comprise a contact between a portion of tip stabilization mechanism 110 and a portion of valved cannula 1050, e.g., a valved cannula contact 1110 may comprise a contact between tip stabilization mechanism proximal end 112 and valve hinge superior surface 1066. Illustratively, a valved cannula contact 1110 may be configured to apply a force to fixation mechanism 130, e.g., a valved cannula contact 1110 may apply a normal force to tip stabilization mechanism 110. In one or more embodiments, an application of a normal force to tip stabilization mechanism 110 may be configured to retract tip stabilization mechanism 110 relative to hypodermic tube 230, e.g., a normal force applied to tip stabilization mechanism 110 may be greater than a static friction force between fixation mechanism 130 and hypodermic tube 230. Illustratively, an application of a normal force to tip stabilization mechanism 110 may not be configured to retract tip stabilization mechanism 110 relative to hypodermic tube 230, e.g., a normal force applied to tip stabilization mechanism 110 may be less than a static friction force between fixation mechanism 130 and hypodermic tube 230.

Figure 11C:
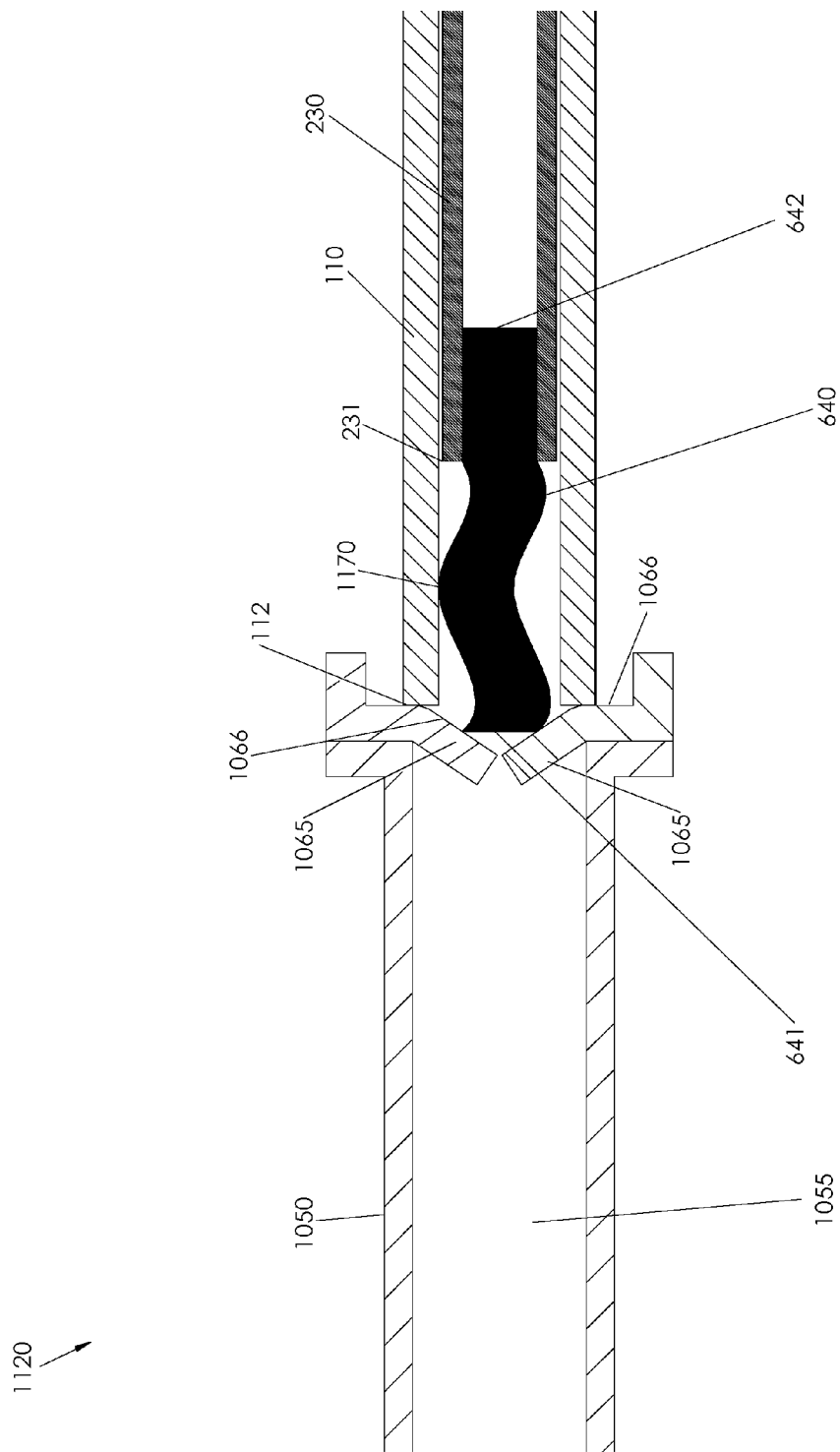

FIG. 11C illustrates an irrigating and aspirating tip stabilization 1120. Illustratively, a surgeon may actuate hypodermic tube 230 towards inner lumen 1055 after a valved cannula contact 1110, e.g., a surgeon may actuate hypodermic tube distal end 231 towards inner lumen 1055 after a valved cannula contact 1110. In one or more embodiments, actuating hypodermic tube 230 towards inner lumen 1055 after a valved cannula contact 1110 may be configured to apply a force to tip stabilization mechanism 110, e.g., actuating hypodermic tube distal end 231 towards inner lumen 1055 after a valved cannula contact 1110 may be configured to apply a force to tip stabilization mechanism proximal end 112. Illustratively, an application of a force to tip stabilization mechanism 110 may be configured to actuate tip stabilization mechanism 110 relative to housing tube 230, e.g., an application of a force to tip stabilization mechanism proximal end 112 that is greater than a force of static friction between fixation mechanism 130 and hypodermic tube 230 may be configured to retract tip stabilization mechanism 110 relative to hypodermic tube 230. Illustratively, an application of a force to tip stabilization mechanism proximal end 112 may be configured to actuate tip stabilization mechanism distal end 111 towards hypodermic tube proximal end 232. In one or more embodiments, an actuation of tip stabilization mechanism 110 relative to housing tube 230 may be configured to expose a portion of irrigating and aspirating tip 640, e.g., an actuation of tip stabilization mechanism distal end 111 towards hypodermic tube proximal end 232 may be configured to expose irrigating and aspirating tip distal end 641. Illustratively, an exposure of a portion of irrigating and aspirating tip 640 may be configured to facilitate a contact between irrigating and aspirating tip 640 and valve hinge superior surface 1066, e.g., an exposure of a portion of irrigating and aspirating tip 640 may be configured to facilitate a contact between irrigating and aspirating tip distal end 641 and valve hinge superior surface 1066. In one or more embodiments, as a surgeon actuates hypodermic tube distal end 231 towards inner lumen 1055, a contact between irrigating and aspirating tip 640 and valve hinge superior surface 1066 may be configured to cause irrigating and aspirating tip 640 to deform, e.g., a contact between irrigating and aspirating tip 640 and valve hinge superior surface 1066 may be configured to cause irrigating and aspirating tip 640 to bend or flex. Illustratively, a contact between irrigating and aspirating tip 640 and valve hinge superior surface 1066 may be configured to cause an elastic deformation of irrigating and aspirating tip 640. In one or more embodiments, a contact between irrigating and aspirating tip 640 and valve hinge superior surface 1066 may be configured to cause a plastic deformation of irrigating and aspirating tip 640.

Illustratively, tip stabilization mechanism 110 may be configured to facilitate an irrigating and aspirating tip deformation prevention 1170, e.g., tip stabilization mechanism inner diameter 114 may be configured to prevent irrigating and aspirating tip 640 from deforming. In one or more embodiments, tip stabilization mechanism 110 may be configured to prevent a portion of irrigating and aspirating tip 640 from deforming beyond a line tangent to a wall of inner lumen 1055, e.g., tip stabilization mechanism inner diameter 114 may be configured to prevent a portion of irrigating and aspirating tip 640 from deforming beyond a line tangent to a wall of inner lumen 1055. For example, tip stabilization mechanism 110 may be configured to prevent a portion of irrigating and aspirating tip 640 from bending or flexing beyond a line tangent to a wall of inner lumen 1055. Illustratively, tip stabilization mechanism 110 may be configured to prevent a portion of irrigating and aspirating tip 640 from deforming beyond a line tangent to an outer diameter of valved cannula 1050, e.g., tip stabilization mechanism inner diameter 114 may be configured to prevent a portion of irrigating and aspirating tip 640 from deforming beyond a line tangent to an outer diameter of valved cannula 1050. For example, tip stabilization mechanism 110 may be configured to prevent a portion of irrigating and aspirating tip 640 from bending or flexing beyond a line tangent to an outer diameter of valved cannula 1050. In one or more embodiments, an irrigating and aspirating tip deformation prevention 1170 may be configured to actuate valve hinge 1065, e.g., an irrigating and aspirating tip deformation prevention 1170 may be configured to separate a first valve hinge 1065 and a second valve hinge 1065 at valve hinge interface 1060. Illustratively, an irrigating and aspirating tip deformation prevention 1170 may be configured to guide a portion of irrigating and aspirating tip 640 into inner lumen 1055, e.g., a membrane removing tip deformation prevention 1070 may be configured to guide irrigating and aspirating tip distal end 641 into inner lumen 1055. In one or more embodiments, irrigating and aspirating tip 640 may have a first stiffness, valve hinge 1065 may have a second stiffness, and tip stabilization mechanism 110 may have a third stiffness wherein the second stiffness is greater than the first stiffness and the third stiffness is greater than the second stiffness. Illustratively, the second stiffness of valve hinge 1065 may be configured to cause a deformation of irrigating and aspirating tip 640 and the third stiffness of tip stabilization mechanism 110 may be configured to guide a portion of irrigating and aspirating tip 640 into inner lumen 1055.

Figure 11D:
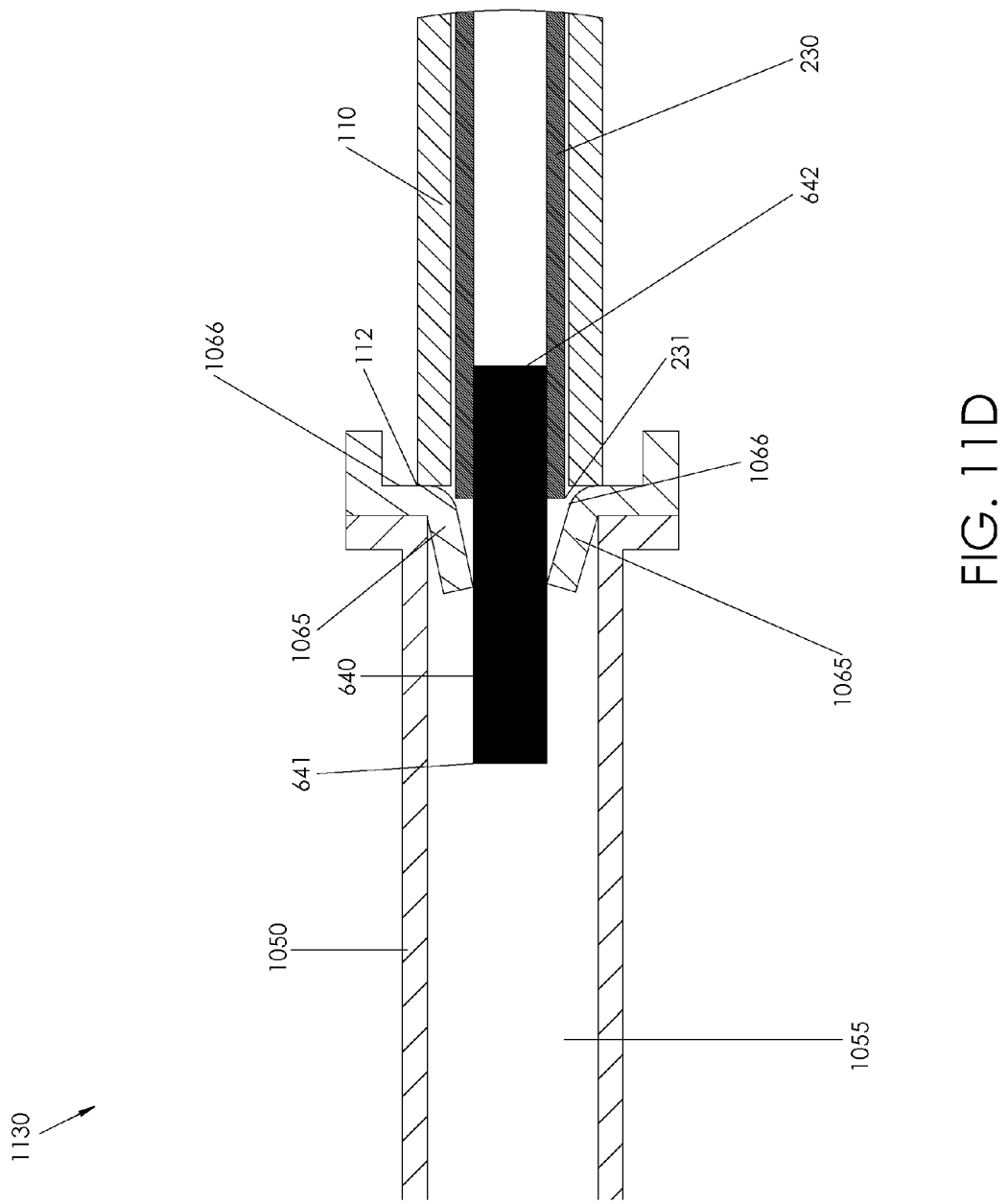

FIG. 11D illustrates a partial valved cannula ingress 1130. Illustratively, a surgeon may actuate hypodermic tube 230 towards inner lumen 1055 after an irrigating and aspirating tip stabilization 1120, e.g., a surgeon may actuate hypodermic tube distal end 231 towards inner lumen 1055 after an irrigating and aspirating tip stabilization 1120. In one or more embodiments, an actuation of hypodermic tube distal end 231 towards inner lumen 1055 after an irrigating and aspirating tip stabilization 1120 may be configured to actuate a portion of irrigating and aspirating tip 640 into valved cannula 1050, e.g., an actuation of hypodermic tube distal end 231 towards inner lumen 1055 after an irrigating and aspirating tip stabilization 1120 may be configured to actuate irrigating and aspirating tip distal end 641 into inner lumen 1055. Illustratively, an actuation of hypodermic tube distal end 231 towards inner lumen 1055 after an irrigating and aspirating tip stabilization 1120 may be configured to increase a separation of a first valve hinge 1065 and a second valve hinge 1065. Illustratively, an actuation of hypodermic tube distal end 231 towards inner lumen 1055 after an irrigating and aspirating tip stabilization 1120 may be configured to cause irrigating and aspirating tip 640 to return to its original geometry, e.g., an actuation of hypodermic tube distal end 231 towards inner lumen 1055 after an irrigating and aspirating tip stabilization 1120 may be configured to cause irrigating and aspirating tip 640 to return to its pre-deformation geometry.

Figure 11E:
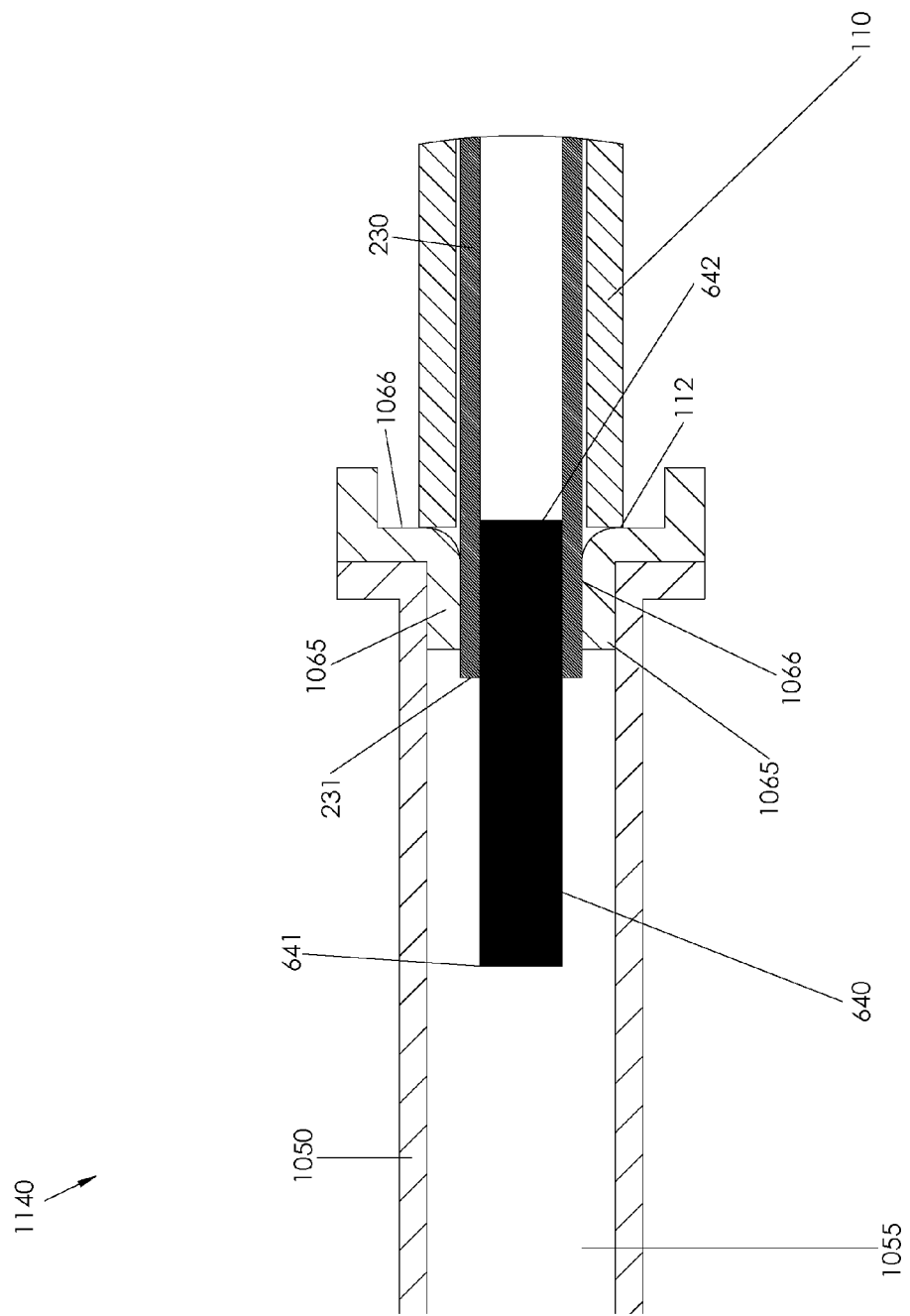

FIG. 11E illustrates a complete valved cannula ingress 1140. Illustratively, a surgeon may actuate hypodermic tube 230 towards inner lumen 1055 after a partial valved cannula ingress 1130, e.g., a surgeon may actuate hypodermic tube distal end 231 into inner lumen 1055 after a partial valved cannula ingress 1130. In one or more embodiments, an actuation of hypodermic tube distal end 231 into inner lumen 1055 after a partial valved cannula ingress 1130 may be configured to fully separate a first valve hinge 1065 and a second valve hinge 1065. Illustratively, an actuation of hypodermic tube distal end 231 into inner lumen 1055 after a partial valved cannula ingress 1130 may be configured to cause a portion of hypodermic tube 230 to contact a portion of valve hinge superior surface 1066, e.g., an actuation of hypodermic tube distal end 231 into inner lumen 1055 after a partial valved cannula ingress 1130 may be configured to cause an outer portion of hypodermic tube 230 to contact a portion of valve hinge superior surface 1066.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a cannula ingress system, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   a hypodermic tube having a hypodermic tube distal end and a hypodermic tube proximal end;
   a tip having a tip distal end and a tip proximal end wherein the tip proximal end is disposed within the hypodermic tube and the tip distal end extends out from the hypodermic tube distal end;
   a tip stabilization mechanism having a tip stabilization mechanism distal end and a tip stabilization mechanism proximal end;
   a fixation mechanism channel of the tip stabilization mechanism;
   a fixation mechanism disposed in the fixation mechanism channel wherein the tip distal end and the hypodermic tube distal end are disposed within an inner bore of the tip stabilization mechanism and the fixation mechanism is configured to temporarily fix the tip stabilization mechanism in a position relative to the hypodermic tube; and an inner diameter of the tip stabilization mechanism and an outer diameter of the tip stabilization mechanism wherein the inner diameter is configured to prevent the tip from deforming.

2. The instrument of claim 1 wherein the tip is colored black to enhance visualization of the tip.

3. The instrument of claim 1 wherein the tip is a membrane removing tip.

4. The instrument of claim 1 wherein the tip is an irrigating and aspirating tip.

5. The instrument of claim 1 further comprising:
a valved cannula;
an inner lumen of the valved cannula;
a first valve hinge of the valved cannula; and
a second valve hinge of the valved cannula.

6. The instrument of claim 5 wherein a contact between the tip distal end and the valved cannula is configured to cause the tip to deform.

7. The instrument of claim 6 wherein the inner diameter of the tip stabilization mechanism is configured to prevent a portion of the tip from deforming beyond a line tangent to a wall of the inner lumen of the valved cannula.

8. The instrument of claim 1 further comprising:
a handle having a handle distal end and a handle proximal end; and
a hypodermic tube housing of the handle wherein the hypodermic tube proximal end is disposed in the hypodermic tube housing.

9. The instrument of claim 1 further comprising:
a flow control mechanism having a flow control mechanism distal end and a flow control mechanism proximal end;
a fluid guide having a fluid guide distal end and a fluid guide proximal end, the fluid guide disposed within the flow control mechanism wherein the fluid guide proximal end is disposed between the flow control mechanism distal end and the flow control mechanism proximal end; and
a hypodermic tube housing of the fluid guide wherein the hypodermic tube proximal end is disposed in the hypodermic tube housing.

10. The instrument of claim 9 further comprising:
a pressure vent of the flow control mechanism; and
a pressure vent tactile locater configured to allow a surgeon to tactilely identify a location of the pressure vent.

11. An instrument comprising:
a hypodermic tube having a hypodermic tube distal end and a hypodermic tube proximal end;
a membrane removing tip having a membrane removing tip distal end and a membrane removing tip proximal end wherein the membrane removing tip proximal end is disposed within the hypodermic tube and the membrane removing tip distal end extends out from the hypodermic tube distal end;
a tip stabilization mechanism having a tip stabilization mechanism distal end and a tip stabilization mechanism proximal end;
a fixation mechanism channel of the tip stabilization mechanism;
a fixation mechanism disposed in the fixation mechanism channel wherein the membrane removing tip distal end and the hypodermic tube distal end are disposed within an inner bore of the tip stabilization mechanism and the fixation mechanism is configured to temporarily fix the tip stabilization mechanism in a position relative to the hypodermic tube; and an inner diameter of the tip stabilization mechanism and an outer diameter of the tip stabilization mechanism wherein the inner diameter is configured to prevent the membrane removing tip from deforming.

12. The instrument of claim 11 wherein the membrane removing tip is colored black to enhance visualization of the membrane removing tip.

13. The instrument of claim 11 further comprising:
a valved cannula;
an inner lumen of the valved cannula;
a first valve hinge of the valved cannula; and
a second valve hinge of the valved cannula.

14. The instrument of claim 13 wherein a contact between the membrane removing tip distal end and the valved cannula is configured to cause the membrane removing tip to deform.

15. The instrument of claim 14 wherein the inner diameter of the tip stabilization mechanism is configured to prevent a portion of the membrane removing tip from deforming beyond a line tangent to a wall of the inner lumen of the valved cannula.

16. An instrument comprising:
a hypodermic tube having a hypodermic tube distal end and a hypodermic tube proximal end;
an irrigating and aspirating tip having an irrigating and aspirating tip distal end and an irrigating and aspirating tip proximal end wherein the irrigating and aspirating tip proximal end is disposed within the hypodermic tube and the irrigating and aspirating tip distal end extends out from the hypodermic tube distal end;
a tip stabilization mechanism having a tip stabilization mechanism distal end and a tip stabilization mechanism proximal end;
a fixation mechanism channel of the tip stabilization mechanism;
a fixation mechanism disposed in the fixation mechanism channel wherein the irrigating and aspirating tip distal end and the hypodermic tube distal end are disposed within an inner bore of the tip stabilization mechanism and the fixation mechanism is configured to temporarily fix the tip stabilization mechanism in a position relative to the hypodermic tube; and
an inner diameter of the tip stabilization mechanism and an outer diameter of the tip stabilization mechanism wherein the inner diameter is configured to prevent the irrigating and aspirating tip from deforming.

17. The instrument of claim 16 wherein the irrigating and aspirating tip is colored black to enhance visualization of the irrigating and aspirating tip.

18. The instrument of claim 16 further comprising:
a valved cannula;
an inner lumen of the valved cannula;
a first valve hinge of the valved cannula; and
a second valve hinge of the valved cannula.

19. The instrument of claim 18 wherein a contact between the irrigating and aspirating tip distal end and the valved cannula is configured to cause the irrigating and aspirating tip to deform.

20. The instrument of claim 19 wherein the inner diameter of the tip stabilization mechanism is configured to prevent a portion of the irrigating and aspirating tip from deforming beyond a line tangent to a wall of the inner lumen of the valved cannula.

\* \* \* \* \*